United States Patent
Okuro et al.

(10) Patent No.: US 7,582,781 B2
(45) Date of Patent: Sep. 1, 2009

(54) OPTICALLY ACTIVE HALOHYDRIN DERIVATIVE AND PROCESS FOR PRODUCING OPTICALLY ACTIVE EPOXY ALCOHOL DERIVATIVE FROM THE SAME

(75) Inventors: Kazumi Okuro, Hyogo (JP); Tatsuyoshi Tanaka, Hyogo (JP); Masaru Mitsuda, Hyogo (JP); Kenji Inoue, Hyogo (JP)

(73) Assignee: Kaneka Corporation, Osaka (JP)

( * ) Notice: Subject to any disclaimer, the term of this patent is extended or adjusted under 35 U.S.C. 154(b) by 665 days.

(21) Appl. No.: 10/563,635

(22) PCT Filed: Jul. 5, 2004

(86) PCT No.: PCT/JP2004/009883

§ 371 (c)(1),
(2), (4) Date: Jan. 6, 2006

(87) PCT Pub. No.: WO2005/007638

PCT Pub. Date: Jan. 27, 2005

(65) Prior Publication Data

US 2006/0155136 A1    Jul. 13, 2006

(30) Foreign Application Priority Data

Jul. 18, 2003 (JP) .............................. 2003-199447
Feb. 19, 2004 (JP) .............................. 2004-042437

(51) Int. Cl.
C07D 301/24 (2006.01)
C07D 301/26 (2006.01)
C07D 405/06 (2006.01)
C07C 33/26 (2006.01)
C07C 69/353 (2006.01)
C07F 7/04 (2006.01)

(52) U.S. Cl. .................... 549/521; 548/268.8; 556/449; 560/254; 568/660; 568/765

(58) Field of Classification Search ................. 549/521; 548/268.8; 556/449; 560/254; 568/660, 568/811
See application file for complete search history.

(56) References Cited

U.S. PATENT DOCUMENTS 4,584,307 A    4/1986    Richardson et al.

2003/0236419 A1    12/2003    Wang et al.
2005/0085521 A1    4/2005    Suzuki et al.

FOREIGN PATENT DOCUMENTS

| EP | 0 332 387 A1 | 9/1989 |
|---|---|---|
| EP | 0 415 748 A1 | 3/1991 |
| EP | 1 535 914 A1 | 6/2005 |
| GB | 2 363 379 A | 12/2001 |
| JP | 10-212287 | 8/1998 |
| JP | 2003-327578 | 11/2003 |

OTHER PUBLICATIONS

Konosu T., et al., "Concise Synthesis of Optically Active Oxirane Precursors for the Preparation of Triazole Antifungals Using the Friedel-Crafts Reaction of (S)-2- Tosyloxypropionyl Chloride," *Tetrahedron Letters*, vol. 32, No. 51, Dec. 16, 1991, pp. 7545-7548.
International Search Report, from Corresponding International Application No. PCT/JP2004/009883, dated Sep. 21, 2004, 3 pages.
International Preliminary Report on Patentability (Chapter I of the Patent Cooperation Treaty) from Corresponding International Application No. PCT/JP2004/009883, dated May 15, 2006, 7 pages.
International Search Report from Corresponding International Application No. PCT/JP00/01336, dated May 30, 2000, 2 pages.
Supplementary Partial European Search Report from Application No. EP 04 74 7351, Jun. 25, 2007, 4 pages.

*Primary Examiner*—Bernard Dentz
(74) *Attorney, Agent, or Firm*—Brinks Hofer Gilson & Lione

(57) ABSTRACT

The present invention provides an industrially safe, easily operable process for producing an optically active epoxy alcohol derivative useful as an intermediate for pharmaceuticals from inexpensively available materials, and also provides a novel halohydrin derivative serving as an important intermediate for the epoxy alcohol derivative. Furthermore, the present invention provides a process for producing an intermediate for a triazole antifungal agent by allowing a halohydrin to react with a triazole sulfonamide, the process including a small number of steps. A process for producing an optically active epoxy alcohol derivative includes allowing an optically active α-substituted propionate derivative to react with a haloacetic acid derivative in the presence of a base to prepare an optically active haloketone derivative, allowing the resulting haloketone derivative to react with an aryl metal compound to stereoselectively prepare a halohydrin derivative, eliminating a substituent for the hydroxy group of the halohydrin derivative, and performing epoxidation with a base. Furthermore, a process for producing an intermediate for a triazole antifungal agent includes allowing a halohydrin derivative to react with a triazole sulfonamide, the process including a small number of steps.

9 Claims, No Drawings

OPTICALLY ACTIVE HALOHYDRIN DERIVATIVE AND PROCESS FOR PRODUCING OPTICALLY ACTIVE EPOXY ALCOHOL DERIVATIVE FROM THE SAME

RELATED APPLICATIONS

This application is a nationalization of PCT application PCT/JP2004/009883 filed on Jul. 5, 2004, claiming priority based on Japanese Application No. 2003-199447 filed on Jul. 18, 2003 and No. 2004-042437 filed on Feb. 19, 2004, the contents of which are incorporated herein by reference in their entirety.

TECHNICAL FIELD

The present invention relates to a novel process for producing an optically active epoxy alcohol derivative that is an important intermediate compound for use in many fields including pharmaceuticals. In addition, the present invention relates to a novel optically active halohydrin derivative that is an important intermediate material for synthesizing the epoxy alcohol derivative. Furthermore, the present invention relates to a process for producing an intermediate for a triazole antifungal agent by allowing an optically active halohydrin to react with a triazole sulfonamide.

BACKGROUND ART

It has been known that 2-aryl-3-methyl-2-[(1H-1,2,4-triazol-1-yl)methyl]oxirane compounds and 2-aryl-3-methyl-1-(1H-1,2,4-triazol-1-yl)-2,4-butanediol compounds, in particular, the compounds in each of which the aryl group at the 2-position is 2,4-difluorophenyl group or 2,5-difluorophenyl group are important intermediates for triazole antifungal agents (Japanese Unexamined Patent Application Publication Nos. 2-191262, 3-128338, 10-306079, and 8-165263 and U.S. Pat. No. 6,300,353).

Examples of processes for producing a 2-aryl-3-methyl-2-[(1H-1,2,4-triazol-1-yl)methyl]oxirane compound include:

(1) a production process including 3 steps using stereoselective osmium oxidation of an optically active allyl chloride derivative as a key reaction, the allyl chloride derivative being prepared through 4 steps from L-lactic acid and 1,3-difluorobenzene (Japanese Unexamined Patent Application Publication No. 2-191262);

(2) a production process including a stereoselective addition reaction of a Grignard reagent to an optically active α-keto alcohol derivative and further 3 to 9 steps, the α-keto alcohol derivative being prepared through 6 steps from L-lactic acid and 1,3-difluorobenzene (Japanese Unexamined Patent Application Publication Nos. 2-191262 and 10-212287);

(3) a production process including stereoselective epoxidation of an optically active α-keto alcohol derivative and further 3 steps, the α-keto alcohol derivative being prepared through 3 steps from D-lactic acid (Japanese Unexamined Patent Application Publication No. 10-306079 and U.S. Pat. No. 6,300,353); and (4) a production process including asymmetric oxidation of an allyl alcohol derivative as a key reaction and further 2 steps, the allyl alcohol derivative being prepared through 7 steps from chloroacetic chloride and 1,3-difluorobenzene, the asymmetric oxidation being developed by Sharpless et al. (Synlett, 1110-1112, 1995).

A 2-aryl-3-methyl-1-(1H-1,2,4-triazol-1-yl)-2,4-butanediol compound is prepared by stereoselective dihydroxylation of a 3-aryl-4-butene-4-alkoxy-1-butene compound as a key reaction and further 3 steps, the 3-aryl-4-butene-4-alkoxy-1-butene compound being prepared through 5 steps from an optically active 3-hydroxy-2-methylpropionate compound (Japanese Unexamined Patent Application Publication No. 8-165263).

A 1,2-epoxy-2-arylbutan-3-ol, which is an optically active 1,2-epoxy alcohol, used as an important material for the above-described 2-aryl-3-methyl-2-[(1H-1,2,4-triazol-1-yl)methyl]oxirane intermediate is produced by a known process of stereoselectively oxidizing an allyl alcohol derivative using tert-butyl hydroperoxide in the presence of a metal catalyst, the allyl alcohol derivative being prepared through at least 4 steps from L-lactic acid and an aromatic compound (Japanese Unexamined Patent Application Publication No. 2-191262).

However, a process for producing a (2R,3S)-2-aryl-3-methyl-1-(1H-1,2,4-triazol-1-yl)-2,4-butane diol has problems with safety and cost because an osmium oxide and dicyclohexylcarbodiimide that are known expensive and highly toxic must be used. Furthermore, the process requires 9 steps starting from an easily available material. That is, there has been no simple process.

The process for producing the optically active 1,2-epoxy alcohol must use a peracid as an oxidant, thus disadvantageously resulting in difficulty in mass production in view of industrial safety. Furthermore, the oxidation is a diastereoselective reaction induced by hydroxy group attached to an asymmetric carbon originated from L-lactic acid. Although there are 2 types of diastereomers (threo-diastereomer and erythro-diastereomer), a compound that can be produced by the process is only the erythro-diastereomer. Therefore, to obtain the threo-diastereomer required for producing an intermediate for a triazole antifungal agent, further 2 steps are required to convert the erythro-diastereomer into the threo-diastereomer of the optically active epoxy alcohol.

The above-described known processes for producing the 2-aryl-3-methyl-2-[(1H-1,2,4-triazol-1-yl)methyl]oxirane compound serving as an intermediate for a triazole antifungal agent have many industrial practical problems as described below: in process (1), an osmium oxide, which is expensive and highly toxic, must be used; in process (2), an osmium oxide must be used as in process (1), and 10 to 15 steps are required starting from a commercially available material; in process (3), a diastereomeric oxirane compound is prepared by the stereoselective epoxidation of an optically active α-ketoalcohol derivative, but column chromatography is used for purifying the resulting diastereomer; and in process (4), the Sharpless asymmetric oxidation must use tert-butyl hydroperoxide, which is a peracid, as an oxygen source.

DISCLOSURE OF INVENTION

With respect to a process for producing an optically active epoxy alcohol derivative, which is an important intermediate in the pharmaceutical field or the like, in view of the above-described problems of the known processes, the present inventors have conducted intensive studies on a process that can be safely operated even in mass production using only a material and an agent that are easy to handle industrially and available inexpensively. As a result, the present inventors have developed a novel process of subjecting an optically active haloketone derivative that can be efficiently prepared through 2 steps from an optically active lactate to highly stereoselective addition reaction with an aryl-metal compound to prepare a structurally novel optically active halohydrin derivative, and subsequently performing 1 or 2 steps to produce an optically active epoxy alcohol derivative. The stereoselectivity in the addition reaction of the aryl-metal compound to the haloketone derivative can be controlled by changing a substituent at the α-position of the haloketone derivative. That is, the production process can produce any desired diastereomer of the optically active halohydrin derivative and is thus widely applicable. Furthermore, by using a haloketone derivative having one more carbon atom than the number of carbon atoms in the above-described haloketone derivative, the production process is more widely applicable.

The epoxy alcohol is allowed to react with triazole to produce a 2-aryl-3-methyl-2-[(1H-1,2,4-triazol-1-yl)methyl]oxirane serving as an intermediate for a triazole antifungal agent. Similarly, an epoxy alcohol obtained from the haloketone derivative having one more carbon atom is also allowed to react with triazole to produce 2-aryl-3-methyl-1-(1H-1,2,4-triazol-1-yl)-2,4-butanediol serving as a useful intermediate for a triazole antifungal agent.

Furthermore, a process for producing a 2-aryl-3-methyl-2-[(1H-1,2,4-triazol-1-yl)methyl]oxirane serving as an intermediate for a triazole antifungal agent in one step of allowing an optically active halohydrin that can be prepared in the present invention to react with triazole sulfonamide was also developed.

The present invention can be widely applied to produce various known intermediates for triazole antifungal agents and is thus useful.

That is, the present invention relates to a process for producing an optically active epoxy alcohol derivative represented by general formula (14):

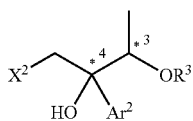

(14)

(wherein $Ar^2$ represents a substituted or unsubstituted aryl group having 6 to 20 carbon atoms; and each of *5 and *6 represents an asymmetric carbon), the process including subjecting a compound represented by general formula (6):

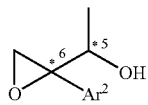

(6)

(wherein $X^2$ represents a halogen atom; $R^3$ represents hydrogen, a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, a substituted or unsubstituted acyl group having 1 to 20 carbon atoms, or a substituted or unsubstituted heterocycle; $Ar^2$ is the same as above; and each of *3 and *4 represents an asymmetric carbon) to at least one treatment selected from acid treatment, fluorine compound treatment, and hydrogenolysis to prepare an optically active halo diol derivative represented by general formula (13):

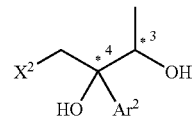

(13)

(wherein $X^2$, $Ar^2$, *3, and *4 are the same as above), and then treating the resulting halo diol derivative with a base; or the process including treating the compound represented by general formula (6) with a base.

The present invention also relates to a process for producing an optically active halohydrin derivative represented by said general formula (6), the process including allowing an optically active haloketone derivative represented by general formula (4):

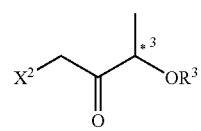

(4)

(wherein $X^2$, $R^3$, and *3 are the same as above) to react with a compound represented by general formula (5):

$Ar^2M^2$ (5)

(wherein $Ar^2$ is the same as above; and $M^2$ represents an alkali metal or a halogenated alkaline-earth metal).

The present invention also relates to a process for producing an optically active halo diol derivative represented by said general formula (13), the process including subjecting a compound represented by general formula (6a):

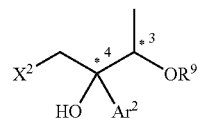

(6a)

(wherein $X^2$, $Ar^2$, *3, and *4 are the same as above; and $R^9$ represents a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, or a substituted or unsubstituted heterocycle) to at least one treatment selected from acid treatment, fluorine compound treatment, and hydrogenolysis.

The present invention also relates to a process for producing an optically active epoxide derivative represented by general formula (16):

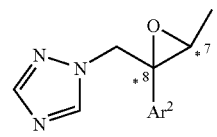

(16)

(wherein Ar² is the same as above; and each of *7 and *8 represents an asymmetric carbon), the process including allowing an optically active halo diol derivative represented by said general formula (13) to react with a compound represented by general formula (15):

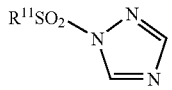
(15)

(wherein R¹¹ represents a substituted or unsubstituted alkyl group having 1 to 18 carbon atoms, a substituted or unsubstituted aryl group having 6 to 20 carbon atoms, or a substituted or unsubstituted aralkyl group having 7 to 20 carbon atoms).

The present invention also relates to a process for producing a compound represented by general formula (17):

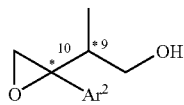
(17)

(wherein Ar² is the same as above; and each of *9, and *10 represents an asymmetric carbon), the process including subjecting a compound represented by general formula (19):

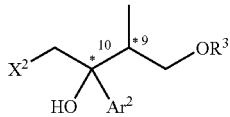
(19)

(wherein X², R³, Ar², *9 and *10 are the same as aboves) to at least one treatment selected from acid treatment, fluorine compound treatment, and hydrogenolysis to prepare an optically active halo diol derivative represented by general formula (20):

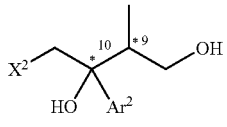
(20)

(wherein X², Ar², *9, and *10 are the same as above), and then treating the resulting diol derivative with a base; or the process including treating the compound represented by general formula (19) with a base.

The present invention also relates to a process for producing an optically active halohydrin derivative represented by said general formula (19), the process including allowing an optically active haloketone derivative represented by general formula (21):

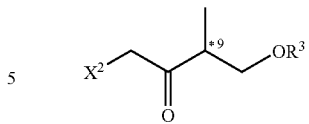
(21)

(wherein X², R³, and *9 are the same as above) to react with the compound represented by said general formula (5).

The present invention also relates to a process for producing an optically active halo diol derivative represented by said general formula (20), the process including subjecting a compound represented by general formula (19a):

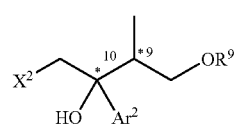
(19a)

(wherein X², Ar², R⁹, *9, and *10 are the same as above) to at least one treatment selected from acid treatment, fluorine compound treatment, and hydrogenolysis.

The present invention also relates to a process for producing an optically active hydroxy compound represented by general formula (12):

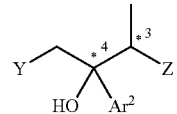
(12)

(wherein Y represents a halogen atom or a substituted or unsubstituted heterocycle; Ar² is the same as above; each of *3 and *4 represents an asymmetric carbon; and Z represents general formula (8):

—O—R⁴ (8)

[wherein R⁴ represents hydrogen, a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, a substituted or unsubstituted acyl group having 1 to 20 carbon atoms, or a substituted or unsubstituted heterocycle], general formula (9):

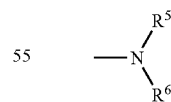
(9)

[wherein R⁵ and R⁶ independently represent hydrogen, a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, a substituted or unsubstituted acyl group having 1 to 20 carbon atoms, a substituted or unsubstituted alkyloxycarbonyl group having 1 to 18 carbon atoms, a substituted or unsubstituted aralkyloxycarbonyl group having 7 to 20 carbon atoms, or a substituted or unsubstituted aryloxycarbonyl group having 6 to 20 carbon atoms], general formula (10):

[wherein R⁷ represents hydrogen, a substituted or unsubstituted alkyl group having 1 to 18 carbon atoms, a substituted or unsubstituted aryl group having 6 to 20 carbon atoms, or a substituted or unsubstituted aralkyl group having 7 to 20 carbon atoms; and n represents an integer of 0 to 2], or general formula (11):

[wherein R⁸ represents hydrogen, a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, a substituted or unsubstituted acyl group having 1 to 20 carbon atoms, or a substituted or unsubstituted heterocycle]), the process including allowing a compound represented by general formula (7):

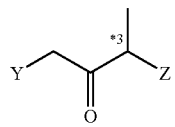

(wherein Y, Z, and *3 are the same as above) to react with the compound represented by said general formula (5).

The present invention also relates to an optically active halohydrin derivative represented by general formula (1):

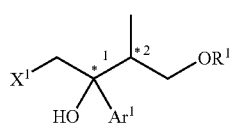

(wherein X¹ represents a halogen atom; Ar¹ represents a substituted or unsubstituted aryl group having 6 to 20 carbon atoms; R¹ represents hydrogen, a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, a substituted or unsubstituted acyl group having 1 to 20 carbon atoms, or a substituted or unsubstituted heterocycle; and each of *1 and *2 represents an asymmetric carbon).

The present invention also relates to an optically active halohydrin derivative represented by general formula (22):

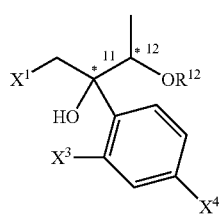

(wherein each of X¹, X³, and X⁴ represents a halogen atom; R¹² represents hydrogen, a substituted or unsubstituted alkyl group having 1 to 18 carbon atoms, a substituted or unsubstituted aryl group having 6 to 20 carbon atoms, a substituted or unsubstituted aralkyl group having 8 to 20 carbon atoms, a substituted or unsubstituted silyl group, or an aliphatic acyl group; and each of *11 and *12 represents an asymmetric carbon).

The present invention also relates to an optically active halohydrin derivative represented by general formula (23):

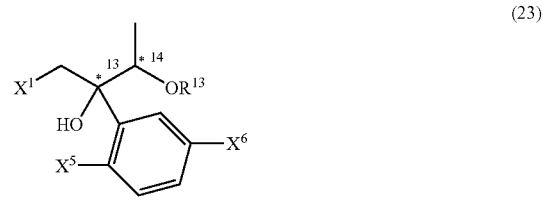

(wherein each of X¹, X⁵, and X⁶ represents a halogen atom; R¹³ represents hydrogen, a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, a substituted or unsubstituted acyl group having 1 to 20 carbon atoms, or a substituted or unsubstituted heterocycle; and each of *13 and *14 represents an asymmetric carbon).

BEST MODE FOR CARRYING OUT THE INVENTION

A step of producing a haloketone derivative represented by general formula (4):

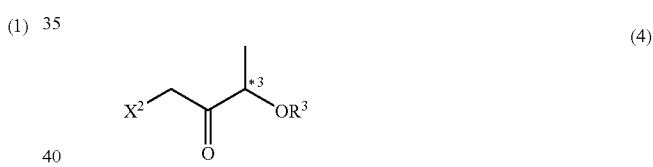

will be described. The step includes allowing a propionate compound represented by general formula (2):

to react with an enolate which is prepared by reaction of a haloacetic acid derivative represented by general formula (3):

with a base, and then subjecting the resulting compound to acid treatment.

A commercially available L-lactate or D-lactate may be directly used as the propionate derivative (2) used in this step. Alternatively, according to need, an L-lactate or D-lactate in which the hydroxy group is replaced with a substituent by a general method known as a typical technique (for example, a method described in Protective Groups in Organic Synthesis, third edition) may also be used.

In the formula, $R^2$ represents an alkyl group, an aryl group, or an aralkyl group. Individual groups will be described. The number of carbon atoms described in this specification does not include the number of carbon atoms in a substituent.

Examples of the alkyl group include substituted or unsubstituted alkyl groups having 1 to 18 carbon atoms, for example, methyl group, ethyl group, n-propyl group, isopropyl group, n-butyl group, isobutyl group, sec-butyl group, tert-butyl group, n-pentyl group, isopentyl group, and n-hexyl group. Examples of the aryl group include substituted or unsubstituted aryl groups having 6 to 20 carbon atoms, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group, and 4-bromophenyl group. Examples of the aralkyl group include substituted or unsubstituted aralkyl groups having 7 to 20 carbon atoms, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group, and 2-phenylpropyl group. Among these, an alkyl group is preferable, and methyl group or ethyl group is more preferable.

$R^3$ represents hydrogen, an alkyl group, an aryl group, an aralkyl group, a silyl group, an acyl group, or a heterocycle. Examples of the alkyl group include substituted or unsubstituted alkyl groups having 1 to 18 carbon atoms, for example, methyl group, ethyl group, n-propyl group, isopropyl group, n-butyl group, isobutyl group, sec-butyl group, tert-butyl group, n-pentyl group, isopentyl group, and n-hexyl group. Examples of the aryl group include substituted or unsubstituted aryl groups having 6 to 20 carbon atoms, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group, and 4-bromophenyl group. Examples of the aralkyl group include substituted or unsubstituted aralkyl groups having 7 to 20 carbon atoms, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group, and 2-phenylpropyl group. The silyl group represents a silyl group in which 0 to 3 groups independently selected from a substituted or unsubstituted alkyl group having 1 to 18 carbon atoms, a substituted or unsubstituted aryl group having 6 to 20 carbon atoms, and a substituted or unsubstituted aralkyl group having 7 to 20 carbon atoms are bonded to silicon. Examples of the alkyl group, the aryl group, and the aralkyl group include the respective groups described above. Specific examples of the silyl group include trimethylsilyl group, triethylsilyl group, tripropylsilyl group, triisopropylsilyl group, tert-butyldimethylsilyl group, dimethylphenylsilyl group, ethyldimethylsilyl group, dimethylpropylsilyl group, dimethylisopropylsilyl group, and triphenylsilyl group. Examples of the acyl group include substituted or unsubstituted acyl groups having 1 to 20 carbon atoms, for example, acetyl group, ethylcarbonyl group, propylcarbonyl group, isopropylcarbonyl group, butylcarbonyl group, isobutylcarbonyl group, sec-butylcarbonyl group, pivaloyl group, pentylcarbonyl group, isopentylcarbonyl group, benzoyl group, 4-methylphenylbenzoyl group, and 4-methoxybenzoyl group. Examples of the heterocycle include tetrahydropyranyl group, tetrahydrofuranyl group, tetrahydrothiopyranyl group, 4-methoxytetrahydropyranyl group, and 1,4-dioxan-2-yl group. Among these, a silyl group, an acyl group, or a heterocycle is preferable. Tert-butyldimethylsilyl group is more preferable as the silyl group. Pivaloyl group is more preferable as the acyl group. Tetrahydropyranyl group is more preferable as the heterocycle. Pivaloyl group is particularly preferable.

The asymmetric carbon represented by *3 may have the R absolute configuration or S absolute configuration but preferably has R configuration.

In formula (3), $X^2$ represents a halogen atom. Examples thereof include a fluorine atom, a chlorine atom, a bromine atom, and an iodine atom. A chlorine atom or a bromine atom is preferable. A chlorine atom is more preferable.

In formula (3), $M^1$ represents hydrogen, an alkali metal, or a halogenated alkaline-earth metal. Examples thereof include, but are not limited to, hydrogen, lithium, sodium, potassium, chloromagnesium, bromomagnesium, and chlorocalcium. Sodium or chloromagnesium is preferable. Sodium is more preferable.

Accordingly, preferable examples of the haloacetic acid derivative (3) include sodium chloroacetate and sodium bromoacetate.

The amount of the haloacetic acid derivative (3) used is 1 to 10 molar equivalents and preferably 1 to 3 molar equivalents relative to the propionate derivative (2).

Examples of the base used in generating the enolate from the haloacetic acid derivative (3) include, but are not particularly limited to, metal amides, such as lithium amide, sodium amide, lithium diisopropylamide, chloromagnesium diisopropylamide, bromomagnesium diisopropylamide, and chloromagnesium dicyclohexylamide; alkyl metals, such as methyllithium, n-butyllithium, methylmagnesium bromide, isopropylmagnesium chloride, and tert-butylmagnesium chloride; metal alkoxides, such as sodium methoxide, magnesium ethoxide, and potassium tert-butoxide; and metal hydride, such as lithium hydride, sodium hydride, potassium hydride, and calcium hydride. Among these, tert-butylmagnesium chloride is preferable.

The amount of the base used is 1 to 10 molar equivalents and preferably 2 to 5 molar equivalents relative to the propionate derivative (2).

In this step, the presence of an amine in addition to the base when allowing the enolate (3) to react with the propionate derivative (2) may increase yield.

The amine is not particularly limited but is preferably a tertiary amine. Examples thereof include alkylamines, such as triethylamine, tributylamine, diisopropylethylamine, trioctylamine, N-methylmorpholine, N-methylpyrrolidine, and N-methylpiperidine; arylamines, such as dimethylaniline and diethylaniline; and aromatic amines, such as pyridine and quinoline. Triethylamine is more preferable.

The amount of the amine used is 1 to 5 molar equivalents and preferably 1 to 3 molar equivalents relative to the propionate derivative (2).

In this step, the haloacetic acid derivative (3), the base, the propionate derivative (2), and the amine may be mixed in any order. For example, by adding dropwise a base solution into a mixed solution of the haloacetic acid derivative (3), the propionate derivative (2), and the amine, the preparation of the enolate and the reaction of the enolate with the propionate derivative (2) can be performed at the same time.

A reaction solvent used in this step is not particularly limited. When a metal amide or an alkali metal salt is used as the base, an aprotic solvent is preferably used. Examples of the aprotic solvent include hydrocarbon solvents, such as benzene, toluene, n-hexane, and cyclohexane; ether solvents, such as diethyl ether, tetrahydrofuran (THF), 1,4-dioxane, tert-butyl methyl ether, dimethoxyethane, and ethylene glycol dimethyl ether; halogenated solvents, such as methylene chloride, chloroform, and 1,1,1-trichloroethane; and amide solvents, such as N,N-dimethylformamide (DMF) and N-methyl-2-pyrrolidone (NMP). THF is preferable. These may be used alone or in combination of two or more.

The reaction temperature is usually within the range of −100° C. to 120° C. A preferable reaction temperature varies depending on the types of base and solvent used but is within the range of −20° C. to 60° C.

In this step, after the completion of the reaction of the compound (2) and the enolate, acid treatment is performed to produce a compound represented by said general formula (4). An acid used in the acid treatment should be a general inorganic acid or organic acid. Examples thereof include, but are not particularly limited to, hydrochloric acid, sulfuric acid, nitric acid, acetic acid, and citric acid.

The temperature at which the acid treatment is performed is not particularly limited but is suitably in the range of −20° C. to 60° C. The amount of the acid used is 1 molar equivalent to 100 molar equivalents, preferably 1 molar equivalent to 50 molar equivalents, and more preferably 1 molar equivalent to 20 molar equivalents relative to the base.

After the reaction in this step, the product represented by said general formula (4) can be obtained by extraction with an organic solvent, such as ethyl acetate, ether, hexane, or toluene. According to need, the product can be purified and isolated by chromatography, crystallization, distillation, or the like. Alternatively, the product may be subjected to a next step without purification.

A step of producing an optically active halohydrin derivative represented by general formula (6):

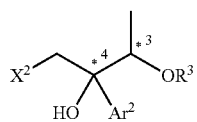

(6)

by allowing the haloketone derivative represented by said general formula (4) to react with a compound represented by general formula (5):

Ar²M²    (5)

will be described below.

In formulae (4) and (6), R³, X², and *3 are the same as above, and *4 represents an asymmetric carbon.

In formula (5), Ar² represents a substituted or unsubstituted aryl group having 6 to 20 carbon atoms. Examples thereof include phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 3-nitrophenyl group, 2-nitrophenyl group, 4-phenylphenyl group, 4-chlorophenyl group, 4-bromophenyl group, 4-fluorophenyl group, 3-fluorophenyl group, 2-fluorophenyl group, 2,3-difluorophenyl group, 2,4-difluorophenyl group, 2,5-difluorophenyl group, 3,4-difluorophenyl group, 2,3-dimethylphenyl group, 2,4-dimethylphenyl group, and 3,4-dimethylphenyl group. 4-fluorophenyl group, 3-fluorophenyl group, 2-fluorophenyl group, 2,3-difluorophenyl group, 2,4-difluorophenyl group, 2,5-difluorophenyl group, or 3,4-difluorophenyl group is preferable. 2,4-difluorophenyl group or 2,5-difluorophenyl group is more preferable.

M² represents an alkali metal or a halogenated alkaline-earth metal. Specific examples thereof include, but are not limited to, lithium, sodium, potassium, chloromagnesium, bromomagnesium, and chlorocalcium. Lithium, chloromagnesium, or bromomagnesium is preferable. Chloromagnesium or bromomagnesium is more preferable.

The compound (5) is commercially available. Alternatively, the compound (5) can be prepared by a known method (for example, Tetrahedron Letters, 42, 3331, 2001) from the corresponding aromatic halide and either the corresponding metal or metal compound. The amount of the compound (5) used is 0.5 to 5.0 molar equivalents and preferably 1.0 to 3.0 molar equivalents relative to the haloketone compound (4).

The reaction temperature is usually within the range of −100° C. to 50° C. A preferable reaction temperature varies depending on the type of a solvent described below but is preferably −20° C. to 30° C.

The reaction time varies depending on the reaction temperature but is usually 0.5 to 36 hours and preferably 1.0 to 24 hours.

A reaction solvent used in this step is not particularly limited but is preferably an aprotic solvent. Examples of the aprotic solvent include hydrocarbon solvents, such as benzene, toluene, n-hexane, and cyclohexane; ether solvents, such as diethyl ether, tetrahydrofuran (THF), 1,4-dioxane, tert-butyl methyl ether, dimethoxyethane, and ethylene glycol dimethyl ether; halogenated solvents, such as methylene chloride, chloroform, and 1,1,1-trichloroethane; and amide solvents, such as N,N-dimethylformamide (DMF) and N-methyl-2-pyrrolidone (NMP). THF, toluene, or hexane is preferable. These may be used alone or in combination of two or more.

In this step, the addition method and the order of addition of the compound (4), the compound (5), and the reaction solvent are not particularly limited.

The asymmetric carbon represented by *3 may have the R absolute configuration or S absolute configuration. Similarly, the asymmetric carbon represented by *4 may have the R absolute configuration or S absolute configuration. The asymmetric carbon represented by *3 preferably has R configuration, and the asymmetric carbon represented by *4 preferably has S configuration.

After the reaction in this step, the product (6) can be obtained by extraction with an organic solvent such as ethyl acetate, ether, hexane, or toluene.

This reaction usually proceeds highly stereoselectively to produce the optically active halohydrin derivative (6) with high diastereomeric ratio depending on the type of substituent.

Furthermore, according to need, purification and isolation can be performed by chromatography, crystallization, distillation, or the like. Alternatively, the product may be subjected to a next step without purification and isolation.

Furthermore, the compound (6) is usually formed as a diastereomeric mixture. Thus, according to need, the diastereomeric excess can be suitably increased by crystallization. The diastereomeric excess is defined by; (diastereomer A content−diastereomer B content)/(diastereomer A content+ diastereomer B content)×100%

A solvent used for the crystallization varies depending on the compound and thus is not particularly limited. Examples thereof include pentane, hexane, heptane, octane, water, methanol, ethanol, n-propanol, isopropanol, n-butanol, isobutanol, tert-butanol, benzene, xylene, trimethylbenzene, tetrahydrofuran, tetrahydropyran, 1,3-dioxane, 1,4-dioxane, methyl acetate, ethyl acetate, n-propyl acetate, isopropyl acetate, n-butyl acetate, isobutyl acetate, tert-butyl acetate, dimethyl ether, tert-butyl methyl ether, acetonitrile, propionitrile, butyronitrile, acetone, DMF, DMSO, and N-methyl-2-pyrrolidone (NMP); and a mixed solvent of two or more of these.

A process for producing an optically active epoxy alcohol derivative represented by general formula (14):

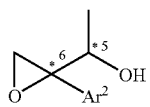

(14)

will now be described. The process includes subjecting a compound represented by said general formula (6) to at least one treatment selected from acid treatment, fluorine compound treatment, and hydrogenolysis to prepare an optically active halo diol derivative represented by general formula (13):

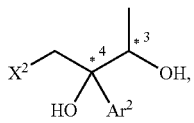

(13)

and then subjecting the resulting halo diol derivative to base treatment; or the process includes subjecting the compound represented by said general formula (6) to base treatment.

In the formulae, $Ar^2$, $X^2$, $R^3$, *3, and *4 are the same as above, and each of *5 and *6 represents an asymmetric carbon.

When $R^3$ in the said general formula (6) represents a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, or a substituted or unsubstituted heterocycle, an optically active epoxy alcohol derivative represented by general formula said (14) is preferably produced by subjecting the compound (6) to at least one treatment selected from acid treatment, fluorine compound treatment, and hydrogenolysis to prepare an optically active halo diol derivative represented by said general formula (13), and then subjecting the resulting halo diol derivative to base treatment. The process will be described in detail below.

In converting the compound (6) into the compound (13), one of acid treatment, fluorine compound treatment, and hydrogenolysis can be employed with reference to a method described in, for example, "Protective Groups in Organic Synthesis, third edition". Examples of an acid used in the acid treatment include hydrochloric acid, sulfuric acid, nitric acid, acetic acid, trifluoroacetic acid, toluenesulfonic acid, methanesulfonic acid, and ammonium chloride. Hydrochloric acid, sulfuric acid, or ammonium chloride is preferable.

Examples of a fluorine compound used in the fluorine compound treatment include tetrabutylammonium fluoride (TBAF), potassium fluoride, sodium fluoride, lithium fluoride, and cesium fluoride. TBAF, potassium fluoride, or sodium fluoride is preferable. The hydrogenolysis should be performed with a compound serving as a hydrogen source, such as, hydrogen, formic acid, or ammonium formate, using a noble metal compound, such as a palladium compound, a platinum compound, a rhodium compound, or a ruthenium compound.

When $R^3$ represents a silyl group, the acid treatment or the fluorine compound treatment is preferable. When $R^3$ represents an alkyl group, an aralkyl group, or an aryl group, the acid treatment or the hydrogenolysis is preferable. When $R^3$ represents a heterocycle, the acid treatment is preferable.

After the reaction in this step, the product (13) can be obtained by extraction with an organic solvent, such as ethyl acetate, ether, hexane, or toluene.

According to need, purification and isolation can be performed by chromatography, crystallization, or distillation, or the like. Alternatively, the product may be subjected to a next step without purification.

A solvent used for the crystallization varies depending on the compound and thus is not particularly limited. Examples thereof include pentane, hexane, heptane, octane, water, methanol, ethanol, n-propanol, isopropanol, n-butanol, isobutanol, tert-butanol, benzene, xylene, trimethylbenzene, tetrahydrofuran, tetrahydropyran, 1,3-dioxane, 1,4-dioxane, methyl acetate, ethyl acetate, n-propyl acetate, isopropyl acetate, n-butyl acetate, isobutyl acetate, tert-butyl acetate, dimethyl ether, tert-butyl methyl ether, acetonitrile, propionitrile, butyronitrile, acetone, DMF, DMSO, and N-methyl-2-pyrrolidone (NMP); and a mixed solvent of two or more of these.

A step of converting the halo diol represented by said general formula (13) into the optically active epoxy alcohol derivative represented by said general formula (14) will be described below.

Examples of the base used in the reaction include, but are not particularly limited to, inorganic bases and organic bases. Examples of the inorganic base include lithium hydroxide, sodium hydroxide, potassium hydroxide, potassium carbonate, sodium carbonate, and lithium carbonate. Examples of the organic base include sodium acetate, potassium acetate, lithium acetate, sodium methoxide, lithium methoxide, potassium methoxide, sodium ethoxide, potassium tert-butoxide, triethylamine, and diisopropylethylamine. Lithium hydroxide, sodium hydroxide, potassium hydroxide, lithium methoxide, sodium methoxide, or potassium methoxide is preferable. Lithium hydroxide, sodium hydroxide, or potassium hydroxide is more preferable.

The amount of the base used is 1.0 to 10.0 molar equivalents and preferably 1.0 to 5.0 molar equivalents relative to the compound (13).

Examples of the reaction solvent include, but are not particularly limited to, benzene, toluene, diethyl ether, tetrahydrofuran (THF), 1,4-dioxane, methyl tert-butyl ether, dimethylformamide (DMF), N-methyl-2-pyrrolidone (NMP), DMSO, methanol, ethanol, isopropanol, and water. These may be used alone or in combination of two or more.

The addition method and the order of addition of the compound (13), the base, and the reaction solvent are not particularly limited.

The reaction temperature is usually within the range of −20° C. to 60° C. A preferable reaction temperature varies depending on the types of base and solvent used but is within the range of −10° C. to 50° C.

The asymmetric carbon represented by *5 may be R absolute configuration or S absolute configuration. Similarly, the asymmetric carbon represented by *6 may have the R absolute configuration or S absolute configuration. The asymmetric carbon represented by *5 preferably has R configuration, and the asymmetric carbon represented by *6 preferably has R configuration.

When $R^3$ in said general formula (6) represents hydrogen or a substituted or unsubstituted acyl group having 1 to 20 carbon atoms, an optically active epoxy alcohol derivative represented by said general formula (14) is preferably produced by subjecting the compound (6) to base treatment. The process will be described in detail below.

Examples of the base used include, but are not particularly limited to, inorganic bases, such as tetrabutylammonium hydroxide, lithium hydroxide, sodium hydroxide, potassium hydroxide, potassium carbonate, sodium carbonate, and lithium carbonate and organic bases, such as sodium acetate, potassium acetate, lithium acetate, sodium methoxide, lithium methoxide, potassium methoxide, sodium ethoxide, potassium tert-butoxide, triethylamine, and diisopropylethylamine. Tetrabutylammonium hydroxide, sodium methoxide, lithium methoxide, potassium methoxide, sodium ethoxide, or potassium tert-butoxide is particularly preferable.

The amount of the base used is 1.0 to 10.0 molar equivalents and preferably 1.0 to 5.0 molar equivalents relative to the compound (6).

Examples of the reaction solvent include, but are not particularly limited to, benzene, toluene, diethyl ether, tetrahydrofuran (THF), 1,4-dioxane, tert-butyl methyl ether, dimethylformamide (DMF), N-methyl-2-pyrrolidone (NMP), DMSO, methanol, ethanol, isopropanol, and water. These may be used alone or in combination of two or more.

The reaction temperature is usually within the range of −20° C. to 60° C. A preferable reaction temperature varies depending on the types of base and solvent used but is within the range of −10° C. to 50° C.

The addition method and the order of the compound (6), the base, and the reaction solvent are not particularly limited.

The product (14) can be obtained by extraction with an organic solvent, such as ethyl acetate, ether, hexane, or toluene. According to need, purification and isolation can be performed by chromatography, crystallization, or distillation.

A process for producing a compound represented by said general formula (13) from a compound represented by general formula (6a):

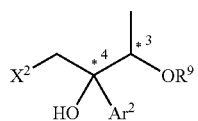

(6a)

will be described below.

In said general formula (6a), $X^2$, $Ar^2$, *3, and *4 are the same as above. Examples of $R^9$ include an alkyl group, an aryl group, an aralkyl group, a silyl group, and a heterocycle.

Examples of the alkyl group include substituted or unsubstituted alkyl groups having 1 to 18 carbon atoms, for example, methyl group, ethyl group, n-propyl group, isopropyl group, n-butyl group, isobutyl group, sec-butyl group, tert-butyl group, n-pentyl group, isopentyl group, and n-hexyl group. Examples of the aryl group include substituted or unsubstituted aryl groups having 6 to 20 carbon atoms, for example, phenyl group, 1-naphthyl group, 2-naphthyl group, 4-methylphenyl group, 3-methylphenyl group, 2-2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group, and 4-bromophenyl group. Examples of the aralkyl group include substituted or unsubstituted aralkyl groups having 7 to 20 carbon atoms, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group, and 2-phenylpropyl group. The silyl group represents a silyl group in which 0 to 3 groups independently selected from a substituted or unsubstituted alkyl group having 1 to 18 carbon atoms, a substituted or unsubstituted aryl group having 6 to 20 carbon atoms, and a substituted or unsubstituted aralkyl group having 7 to 20 carbon atoms are bonded to silicon. Examples of the alkyl group, the aryl group, and the aralkyl group include the respective groups described above. Examples of the silyl group include trimethylsilyl group, triethylsilyl group, tripropylsilyl group, triisopropylsilyl group, tert-butyldimethylsilyl group, dimethylphenylsilyl group, 2-ethyldimethylsilyl group, dimethylpropylsilyl group, dimethylisopropylsilyl group, and triphenylsilyl group.

The heterocycle represents a substituted or unsubstituted heterocycle. Examples thereof include tetrahydropyranyl group, tetrahydrofuranyl group, tetrahydrothiopyranyl group, 4-methoxytetrahydropyranyl group, and 1,4-dioxan-2-yl group.

Among these, a silyl group, or a heterocycle is preferable. Tert-butyldimethylsilyl group is more preferable as the silyl group. Tetrahydropyranyl group is more preferable as the heterocycle.

The reaction from the compound (6a) to the compound (13) can be performed by the same process as that employed in the reaction from the compound (6) to the compound (13).

A step of producing a compound represented by general formula (16):

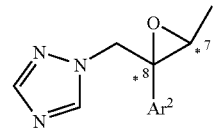

(16)

by allowing a compound represented by said general formula (13) to react with a compound represented by general formula (15):

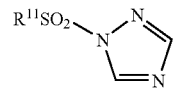

(15)

will be described below.

In formulae (16) and (13), $Ar^2$, $X^2$, *3, and *4 are the same as above, and each of *7 and *8 represents an asymmetric carbon.

The compound represented by said general formula (15) is produced from, for example, triazole and sulfonic acid chloride (J. Am. Chem. Soc., 97, 7332, 1975).

In formula (15), $R^{11}$ represents an alkyl group, an aryl group, or an aralkyl group. Examples of the alkyl group include substituted or unsubstituted alkyl groups having 1 to 18 carbon atoms, for example, methyl group, ethyl groups, n-propyl group, isopropyl group, n-butyl group, isobutyl group, sec-butyl group, tert-butyl group, n-pentyl group, isopentyl group, and n-hexyl group. Examples of the aryl group include substituted or unsubstituted aryl groups having 6 to 20 carbon atoms, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group, and 4-bromophenyl group. Examples of the aralkyl group include substituted or unsubstituted aralkyl groups having 7 to 20 carbon atoms, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group, and 2-phenylpropyl group. The amount of the compound (15) used is 1.0 to 5.0 molar equivalents and preferably 1.0 to 3.0 molar equivalents relative to the compound (13).

The reaction of the compounds represented by said general formulae (13) and (15) is performed in the presence of a base. Examples of the base used include inorganic bases, such as sodium hydride, tetrabutylammonium hydroxide, lithium hydroxide, sodium hydroxide, potassium hydroxide, potassium carbonate, sodium carbonate, and lithium carbonate and organic bases, such as sodium acetate, potassium acetate, lithium acetate, sodium methoxide, lithium methoxide, potassium methoxide, sodium ethoxide, potassium tert-butoxide, n-butyllithium, lithium diisopropylamide, lithium hexamethyldisilazane, potassium hexamethyldisilazane, and sodium hexamethyldisilazane. Sodium hydride or potassium tert-butoxide is particularly preferable.

The amount of the base used is 1.0 to 10.0 molar equivalents, preferably 1.0 to 5.0 molar equivalents, and more preferably 1.0 to 3.0 molar equivalents relative to the compound (13).

Examples of the reaction solvent include, but are not particularly limited to, benzene, toluene, diethyl ether, tetrahydrofuran (THF), 1,4-dioxane, tert-butyl methyl ether, dimethylformamide (DMF), N-methyl-2-pyrrolidone (NMP), and DMSO. These may be used alone or in combination of two or more.

The addition method and the order of addition of the compound (13), the compound (15), the reaction solvent, and the base are not particularly limited.

The reaction temperature is usually within the range of −20° C. to 60° C. A preferable reaction temperature varies depending on the types of base and solvent used but is 0° C. to 50° C.

The product (16) can be obtained by extraction with an organic solvent, such as ethylacetate, ether, hexane, or toluene. According to need, purification and isolation can be performed by chromatography, crystallization, distillation, or the like.

The asymmetric carbon represented by *7 may have R absolute configuration or S absolute configuration. Similarly, the asymmetric carbon represented by *8 may have R absolute configuration or S absolute configuration. The asymmetric carbon represented by *7 preferably has S configuration, and the asymmetric carbon represented by *8 preferably has R configuration.

A step of producing an optically active halohydrin derivative represented by general formula (19):

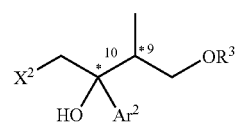

(19)

by allowing a haloketone derivative represented by general formula (21):

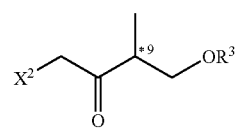

(21)

to react with a compound represented by said general formula (5) will be described below.

In the formulae, $R^3$, $X^2$, $Ar^2$, and $M^2$ are the same as above. Each of *9 and *10 represents an asymmetric carbon that may have R absolute configuration or S absolute configuration.

The compound (21) is available by synthesis from a compound described in WO9623756 and commercially available reagents.

This reaction can be performed using the same reaction solvent and reaction conditions as those in the step of producing the optically active halohydrin derivative represented by said general formula (6) by reaction of the compound represented by said general formula (4) and the compound represented by said general formula (5). Similarly, the compound (19) is subjected to aftertreatment, purification, and isolation under the same conditions as above.

A process for producing a compound represented by general formula (17):

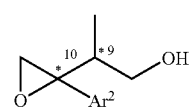

(17)

by subjecting a compound represented by said general formula (19) to at least one treatment selected from acid treatment, fluorine compound treatment, and hydrogenolysis to prepare an optically active halo diol derivative represented by general formula (20):

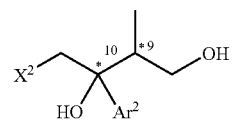

(20)

and then subjecting the resulting halo diol derivative to base treatment; or by subjecting a compound represented by said general formula (19) to base treatment, will be described below.

In the formulae, $X^2$, $Ar^2$, $R^3$, *9, and *10 are the same as above. The production process can be performed using the same reaction solvent and reaction conditions as those in the process for producing the compound represented by said general formula (14) by subjecting the compound represented by said general formula (6) to at least one treatment selected from acid treatment, fluorine compound treatment, and hydrogenolysis to prepare the optically active halo diol derivative represented by said general formula (13) and then subjecting the resulting halo diol derivative to base treatment, or by subjecting the compound represented by said general formula (6) to base treatment. Aftertreatment, purification, and isolation steps can be performed under the same conditions as above.

A process for producing a triazole derivative represented by general formula (18):

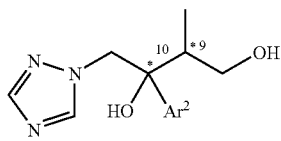
(18)

by allowing the compound represented by said general formula (17) to react with 1,2,4-triazole will be described below.

In the formula, $Ar^2$, *9, and *10 are the same as above.

This reaction is performed in the presence of a base. Examples of the base used include inorganic bases, such as sodium hydride, tetrabutylammonium hydroxide, lithium hydroxide, sodium hydroxide, potassium hydroxide, potassium carbonate, sodium carbonate, and lithium carbonate and organic bases, such as sodium acetate, potassium acetate, lithium acetate, sodium methoxide, lithium methoxide, potassium methoxide, sodium ethoxide, potassium tert-butoxide, n-butyllithium, lithium diisopropylamide, lithium hexamethyldisilazane, potassium hexamethyldisilazane, and sodium hexamethyldisilazane. The inorganic base is preferable. Potassium carbonate, sodium carbonate, or lithium carbonate is more preferable. Potassium carbonate is the most preferable.

The amount of the base used is 1.0 to 10.0 molar equivalents and preferably 1.0 to 5.0 molar equivalents relative to the compound (17).

Examples of the reaction solvent include, but are not particularly limited to, benzene, toluene, diethyl ether, tetrahydrofuran (THF), 1,4-dioxane, tert-butyl methyl ether, dimethylformamide (DMF), N-methyl-2-pyrrolidone (NMP), and DMSO. DMF or DMSO is preferable. DMSO is more preferable. These may be used alone or in combination of two or more.

The reaction temperature is usually within the range of 20° C. to 120° C. A preferable reaction temperature varies depending on the types of base and solvent but is 40° C. to 100° C.

The product (18) can be obtained by extraction with an organic solvent, such as ethyl acetate, ether, hexane, or toluene. According to need, purification and isolation can be performed by chromatography, crystallization, distillation, or the like.

The addition method and the order of addition of the compound (17), 1,2,4-triazole, the base, the reaction solvent are not particularly limited.

A process for producing an optically active halohydrin derivative represented by general formula (12):

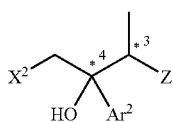
(12)

by allowing a haloketone derivative represented by general formula (7):

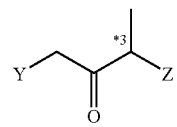
(7)

to react with a compound represented by said general formula (5) will be described below. $Ar^2$, $M^2$, *3, and *4 are the same as above.

Y represents a halogen atom or a substituted or unsubstituted heterocycle.

Examples of the halogen atom include a fluorine atom, a chlorine atom, a bromine atom, and an iodine atom. A chlorine atom or a bromine atom is preferable. A chlorine atom is more preferable.

Examples of the heterocycle include substituted or unsubstituted heterocycles, such as tetrahydropyranyl group, tetrahydrofuranyl group, tetrahydrothienyl group, pyridyl group, pyrazyl group, pyrimidyl group, thienyl group, hydroxypyridyl group, imidazole group, thiazole group, pyrazole group, pyrazolone group, isoxazole group, isothiazole group, pyrrole group, furan group, and triazole group. Triazole group is preferable.

In the formula (7), Z represents general formula (8):

—O—R$^4$ (8)

[wherein R$^4$ represents hydrogen, an alkyl group, an aryl group, an aralkyl group, a silyl group, an acyl group, or a heterocycle], general formula (9):

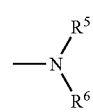
(9)

[wherein, R$^5$ and R$^6$ independently represent hydrogen, an alkyl group, an aryl group, an aralkyl group, a silyl group, an acyl group, an alkyloxycarbonyl group, an aralkyloxycarbonyl group, or an aryloxycarbonyl group], general formula (10):

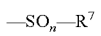
—SO$_n$—R$^7$ (10)

[wherein R$^7$ represents hydrogen, an alkyl group, an aryl group, or an aralkyl group. n represents an integer of 0 to 2], or general formula (11):

—CH$_2$OR$^8$ (11)

[wherein R$^8$ represents hydrogen, an alkyl group, an aryl group, an aralkyl group, a silyl group, an acyl group, or a heterocycle].

In the formulae (8), (9), (10), and (11), examples of the alkyl groups represented by R$^4$, R$^5$, R$^6$, R$^7$, and R$^8$ include substituted or unsubstituted alkyl groups having 1 to 18 carbon atoms, for example, methyl group, ethyl group, n-propyl group, isopropyl group, n-butyl group, isobutyl group, sec-butyl group, tert-butyl group, n-pentyl group, isopentyl group, and n-hexyl group. Examples of the aralkyl group include substituted or unsubstituted aralkyl groups having 7 to 20 carbon atoms, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group, and 2-phenylpropyl group. Examples of the aryl group include substituted or unsubstituted aryl groups having 6 to 20 carbon atoms, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group, and 4-bromophenyl group.

Examples of the silyl groups represented by $R^4$, $R^5$, $R^6$, and $R^8$ include a silyl group in which 0 to 3 groups independently selected from a substituted or unsubstituted alkyl group having 1 to 18 carbon atoms, a substituted or unsubstituted aryl group having 6 to 20 carbon atoms, and a substituted or unsubstituted aralkyl group having 7 to 20 carbon atoms are bonded to silicon. Examples of the alkyl group, the aryl group, and the aralkyl group include the respective groups described above. Specific examples of the silyl group include trimethylsilyl group, triethylsilyl group, tripropylsilyl group, triisopropylsilyl group, tert-butyldimethylsilyl group, dimethylphenylsilyl group, ethyldimethylsilyl group, dimethylpropylsilyl group, dimethylisopropylsilyl group, and triphenylsilyl group.

Examples of the acyl groups represented by $R^4$, $R^5$, $R^6$, and $R^8$ include substituted or unsubstituted acyl groups having 1 to 20 carbon atoms, for example, acetyl group, ethylcarbonyl group, propylcarbonyl group, isopropylcarbonyl group, butylcarbonyl group, isobutylcarbonyl group, sec-butylcarbonyl group, pivaloyl group, pentylcarbonyl group, isopentylcarbonyl group, benzoyl group, 4-methylphenylbenzoyl group, and 4-methoxybenzoyl group.

Examples of the alkyloxycarbonyl group represented by $R^5$ or $R^6$ include alkyl group substituted oxycarbonyl groups having 1 to 18 carbon atoms. The alkyloxycarbonyl group may be substituted or unsubstituted. Examples of the alkyloxycarbonyl group include methoxycarbonyl group, ethoxycarbonyl group, propyloxycarbonyl group, isopropyloxycarbonyl group, butylcarbonyl group, sec-butylcarbonyl group, isobutylcarbonyl group, tert-butyloxycarbonyl group, pentyloxycarbonyl group, isopentyloxycarbonyl group, sec-pentyloxycarbonyl group, tert-pentyloxycarbonyl group, and neopentyloxycarbonyl group. Examples of the aralkyloxycarbonyl group include aralkyl group substituted oxycarbonyl groups having 7 to 20 carbon atoms. The aralkyloxycarbonyl groups may be substituted or unsubstituted. Examples of the aralkyloxycarbonyl group include benzyloxycarbonyl group, 1-phenylethyloxycarbonyl group, 2-phenylethyloxycarbonyl group, 4-methylbenzyloxycarbonyl group, 3-methylbenzyloxycarbonyl group, 2-methylbenzyloxycarbonyl group, 4-methoxybenzyloxycarbonyl group, 3-methoxybenzyloxycarbonyl group, 2-methoxybenzyloxycarbonyl group, 4-chlorobenzyloxycarbonyl group, 3-chlorobenzyloxycarbonyl group, 2-chlorobenzyloxycarbonyl group, 4-cyanobenzyloxycarbonyl group, 3-cyanobenzyloxycarbonyl group, 2-cyanobenzyloxycarbonyl group, 3,4-dimethylbenzyloxycarbonyl group, 2,4-dimethylbenzyloxycarbonyl group, 3,4-dimethoxybenzyloxycarbonyl group, 2,4-dimethoxybenzyloxycarbonyl group, 1-phenylpropyloxycarbonyl group, 2-phenylpropyloxycarbonyl group, and 3-phenylpropyloxycarbonyl group. Examples of the aryloxycarbonyl group include aryl group substituted oxycarbonyl groups having 6 to 20 carbon atoms. The aryloxycarbonyl groups may be substituted or unsubstituted. Examples of the aryloxycarbonyl group include phenyloxycarbonyl group, 1-naphthyloxycarbonyl group, 2-naphthyloxycarbonyl group, 4-methylphenyloxycarbonyl group, 3-methylphenyloxycarbonyl group, 2-methylphenyloxycarbonyl group, 4-methoxyphenyloxycarbonyl group, 3-methoxyphenyloxycarbonyl group, 2-methoxyphenyloxycarbonyl group, 4-nitrophenyloxycarbonyl group, 3-nitrophenyloxycarbonyl group, 2-nitrophenyloxycarbonyl group, 4-chlorophenyloxycarbonyl group, 3-chlorophenyloxycarbonyl group, 2-chlorophenyloxycarbonyl group, 4-bromophenyloxycarbonyl group, 3-bromophenyloxycarbonyl group, 2-bromophenyloxycarbonyl group, 4-cyanophenyloxycarbonyl group, 3-cyanophenyloxycarbonyl group, phenyloxycarbonyl group, and 2-cyanophenyloxycarbonyl group.

Examples of the heterocycles represented by $R^4$ and $R^8$ include substituted or unsubstituted heterocycles, such as tetrahydropyranyl group, tetrahydrofuranyl group, tetrahydrothiopyranyl group, 4-methoxytetrahydropyranyl group, and 1,4-dioxan-2-yl group.

Among these, a silyl group, an acyl group, or a heterocycle is preferable as $R^4$. Among the silyl groups, tert-butyldimethylsilyl group is particularly preferable. Among the acyl groups, pivaloyl group is particularly preferable. Among the heterocycles, tetrahydropyranyl group is particularly preferable. Pivaloyl group is more particularly preferable.

$R^5$ and $R^6$ are not particularly limited. Any combination of the above-described substituents may be used. Preferably, $R^5$ represents hydrogen, and $R^6$ represents benzyloxycarbonyl group, tert-butyloxycarbonyl group, or methyloxycarbonyl group.

$R^7$ preferably represents methyl group or phenyl group.

A silyl group, an acyl group, or a heterocycle is preferable as $R^8$. Among the silyl groups, tert-butyldimethylsilyl group is particularly preferable. Among the acyl groups, pivaloyl group is particularly preferable. Among the heterocycles, tetrahydropyranyl group is preferable.

The reaction can be performed by the same conditions as those in the step of producing the compound (6) by reaction of the compounds (4) and (5) described above.

A halohydrin derivative represented by general formula (1):

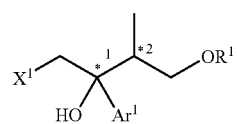

(1)

will be described below. $X^1$ represents a halogen atom. Examples thereof include a fluorine atom, a chlorine atom, a bromine atom, and an iodine atom. A chlorine atom or a bromine atom is preferable. A chlorine atom is more preferable.

$R^1$ represents hydrogen, an alkyl group, an aryl group, an aralkyl group, a silyl group, an acyl group, or heterocycle.

Examples of the alkyl group include substituted or unsubstituted alkyl groups having 1 to 18 carbon atoms, for example, methyl group, ethyl group, n-propyl group, isopropyl group, n-butyl group, isobutyl group, sec-butyl group, tert-butyl group, n-pentyl group, isopentyl group, and n-hexyl group. Examples of the aryl group include substituted or unsubstituted aryl groups having 6 to 20 carbon atoms, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group, and 4-bromophenyl group. Examples of the aralkyl group include substituted or unsubstituted aralkyl groups having 7 to 20 carbon atoms, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group, and 2-phenylpropyl group. The silyl group represents a silyl group in which 0 to 3 groups independently selected from a substituted or unsubstituted alkyl group having 1 to 18 carbon atoms, a substituted or unsubstituted aryl group having 6 to 20 carbon atoms, and a substituted or unsubstituted aralkyl group having 7 to 20 carbon atoms are bonded to silicon. Examples of the alkyl group, the aryl group, and the aralkyl group include the respective groups described above. Specific examples of the silyl group include trimethylsilyl group, triethylsilyl group, tripropylsilyl group, triisopropylsilyl group, tert-butyldimethylsilyl group, dimethylphenylsilyl group, ethyldimethylsilyl group, dimethylpropylsilyl group, dimethylisopropylsilyl group, and triphenylsilyl group. Examples of the acyl group include substituted or unsubstituted acyl groups having 1 to 20 carbon atoms, for example, acetyl group, ethylcarbonyl group, propylcarbonyl group, isopropylcarbonyl group, butylcarbonyl group, isobutylcarbonyl group, sec-butylcarbonyl group, pivaloyl group, pentylcarbonyl group, isopentylcarbonyl group, benzoyl group, 4-methylphenylbenzoyl group, and 4-methoxybenzoyl group. Examples of the heterocycle include substituted or unsubstituted heterocycles, such as tetrahydropyranyl group, tetrahydrofuranyl group, tetrahydrothiopyranyl group, 4-methoxytetrahydropyranyl group, and 1,4-dioxan-2-yl group.

Among these, a silyl group, an acyl group, or a heterocycle is preferable. In the silyl group, tert-butyldimethylsilyl group is more preferable. In the acyl group, pivaloyl group is more preferable. In the heterocycle, tetrahydropyranyl group is more preferable. Pivaloyl group is particularly preferable.

Examples of $Ar^1$ include substituted or unsubstituted aryl groups having 6 to 20 carbon atoms, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 3-nitrophenyl group, 2-nitrophenyl group, 4-phenylphenyl group, 4-chlorophenyl group, 4-bromophenyl group, 4-fluorophenyl group, 3-fluorophenyl group, 2-fluorophenyl group, 2,3-difluorophenyl group, 2,4-difluorophenyl group, 2,5-difluorophenyl group, 3,4-difluorophenyl group, 2,3-dimethylphenyl group, 2,4-dimethylphenyl group, and 3,4-dimethylphenyl group. 4-fluorophenyl group, 3-fluorophenyl group, 2-fluorophenyl group, 2,3-difluorophenyl group, 2,4-difluorophenyl group, 2,5-difluorophenyl group, or 3,4-difluorophenyl group is preferable. 2,4-difluorophenyl group or 2,5-difluorophenyl group is more preferable. The asymmetric carbon represented by *1 may have R absolute configuration or S absolute configuration. Similarly, the asymmetric carbon represented by *2 may have R absolute configuration or S absolute configuration. The compound (1) is a novel compound, and the present inventors found that the compound was useful as an intermediate for a triazole antifungal agent.

A halohydrin derivative compound represented by general formula (22):

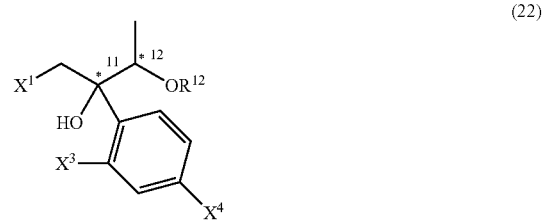

will be described below. $X^1$ is the same as above.

Each of $X^3$ and $X^4$ represents a halogen atom and may be the same or different. Examples thereof include a fluorine atom, a chlorine atom, a bromine atom, and an iodine atom. Preferably, each of X3 and X4 represents a fluorine atom.

$R^{12}$ represents hydrogen, an alkyl group, an aryl group, an aralkyl group, a silyl group, or an aliphatic acyl group.

Examples of the alkyl group include substituted or unsubstituted alkyl groups having 1 to 18 carbon atoms, for example, methyl group, ethyl group, n-propyl group, isopropyl group, n-butyl group, isobutyl group, sec-butyl group, tert-butyl group, n-pentyl group, isopentyl group, and n-hexyl group. Examples of the aryl group include substituted or unsubstituted aryl groups having 6 to 20 carbon atoms, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group, and 4-bromophenyl group. Examples of the aralkyl group include substituted or unsubstituted aralkyl groups having 8 to 20 carbon atoms, for example, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group, and 2-phenylpropyl group. The silyl group represents a silyl group in which 0 to 3 groups independently selected from a substituted or unsubstituted alkyl group having 1 to 18 carbon atoms, a substituted or unsubstituted aryl group having 6 to 20 carbon atoms, and a substituted or unsubstituted aralkyl group having 7 to 20 carbon atoms are bonded to silicon. Examples of the alkyl group, the aryl group, and the aralkyl group include the respective groups described above. Specific examples of the silyl group include trimethylsilyl group, triethylsilyl group, tripropylsilyl group, triisopropylsilyl group, a tert-butyldimethylsilyl group, dimethylphenylsilyl group, ethyldimethylsilyl group, dimethylpropylsilyl group, dimethylisopropylsilyl group, and triphenylsilyl group. Examples of the aliphatic acyl group include acetyl group, ethylcarbonyl group, propylcarbonyl group, isopropylcarbonyl group, butylcarbonyl group, isobutylcarbonyl group, sec-butylcarbonyl group, pivaloyl group, pentylcarbonyl group, and isopentylcarbonyl group.

Among these, a silyl group or an aliphatic acyl group is preferable. Tert-butyldimethylsilyl group is more preferable for the silyl group. Pivaloyl group is more preferable for the aliphatic acyl group. Pivaloyl group is particularly preferable.

The asymmetric carbon represented by *11 may have R absolute configuration or S absolute configuration. Similarly, the asymmetric carbon represented by *12 may have R absolute configuration or S absolute configuration. The asymmetric carbon represented by *11 preferably has S configuration, and the asymmetric carbon represented by *12 preferably has R configuration. The compound (22) having such a configuration is a novel compound, and the present inventors found that the compound was useful as an intermediate for a triazole antifungal agent.

A halohydrin derivative compound represented by general formula (23):

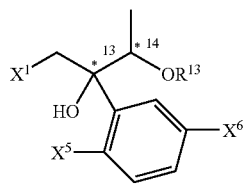

(23)

will be described below. $X^1$ is the same as above.

Each of $X^5$ and $X^6$ represents a halogen atom and may be the same or different. Examples thereof include a fluorine atom, a chlorine atom, a bromine atom, and an iodine atom. Preferably, each of $X^5$ and $X^6$ represents a fluorine atom.

$R^{13}$ represents hydrogen, an alkyl group, an aryl group, an aralkyl group, a silyl group, an acyl group, or heterocycle.

Examples of the alkyl group include substituted or unsubstituted alkyl groups having 1 to 18 carbon atoms, for example, methyl group, ethyl group, n-propyl group, isopropyl group, n-butyl group, isobutyl group, sec-butyl group, tert-butyl group, n-pentyl group, isopentyl group, and n-hexyl group. Examples of the aryl group include substituted or unsubstituted aryl groups having 6 to 20 carbon atoms, for example, phenyl group, 1-naphthyl group, 2-naphthyl group, 4-methylphenyl group, 3-methylphenyl group, 2-methylphenyl group, 4-ethylphenyl group, 3-ethylphenyl group, 4-methoxyphenyl group, 3-methoxyphenyl group, 2-methoxyphenyl group, 4-nitrophenyl group, 4-phenylphenyl group, 4-chlorophenyl group, and 4-bromophenyl group. Examples of the aralkyl group include substituted or unsubstituted aralkyl groups having 7 to 20 carbon atoms, for example, benzyl group, 4-methylbenzyl group, 3-methylbenzyl group, 2-methylbenzyl group, 4-methoxybenzyl group, 3-methoxybenzyl group, 2-methoxybenzyl group, 1-phenylethyl group, 2-phenylethyl group, 1-(4-methylphenyl)ethyl group, 1-(4-methoxyphenyl)ethyl group, 3-phenylpropyl group, and 2-phenylpropyl group. The silyl group represents a silyl group in which 0 to 3 groups independently selected from a substituted or unsubstituted alkyl group having 1 to 18 carbon atoms, a substituted or unsubstituted aryl group having 6 to 20 carbon atoms, or a substituted or unsubstituted aralkyl group having 7 to 20 carbon atoms are bonded to silicon. Examples of the alkyl group, the aryl group, and the aralkyl group include the respective groups described above. Specific examples of the silyl group include trimethylsilyl group, triethylsilyl group, tripropylsilyl group, triisopropylsilyl group, tert-butyldimethylsilyl group, dimethylphenylsilyl group, ethyldimethylsilyl group, dimethylpropylsilyl group, dimethylisopropylsilyl group, and triphenylsilyl group. Examples of the acyl group include substituted or unsubstituted acyl groups having 1 to 20 carbon atoms, for example, acetyl group, ethylcarbonyl group, propylcarbonyl group, isopropylcarbonyl group, butylcarbonyl group, isobutylcarbonyl group, sec-butylcarbonyl group, pivaloyl group, pentylcarbonyl group, isopentylcarbonyl group, benzoyl group, 4-methylphenylbenzoyl group, and 4-methoxybenzoyl group. Examples of the heterocycle include substituted or unsubstituted heterocycles, such as tetrahydropyranyl group, tetrahydrofuranyl group, tetrahydrothiopyranyl group, 4-methoxytetrahydropyranyl group, and 1,4-dioxan-2-yl group.

Among these, a silyl group, an acyl group, or a heterocycle is preferable. Tert-butyldimethylsilyl group is more preferable for the silyl group. Pivaloyl group is more preferable for the acyl group. Tetrahydropyranyl group is more preferable for the heterocycle. Pivaloyl group is particularly preferable.

The asymmetric carbon represented by *13 may have R absolute configuration or S absolute configuration. Similarly, the asymmetric carbon represented by *14 may have R absolute configuration or S absolute configuration. The asymmetric carbon represented by *13 preferably has S configuration, and the asymmetric carbon represented by *14 preferably has R configuration. The compound (23) having such a configuration is a novel compound, and the present inventors found that the compound was useful as an intermediate for a triazole antifungal agent.

EXAMPLES

The present invention will be described in further detail on the basis of examples. However, the present invention is not limited to these examples.

Example 1

(R)-1-Chloro-3-hydroxybutan-2-one

A mixture of 6.25 g (60 mmol) of (R)-methyl lactate, 10.49 g (90 mmol) of sodium chloroacetate, 9.09 g (90 mmol) of triethylamine, and 250 mL of THF was cooled in ice, and 137 g (240 mmol) of a 1.75 M solution of tert-butylmagnesium chloride was added dropwise thereto over a period of 2 hours. After the completion of the dropwise addition, the reaction was allowed to proceed at room temperature for another 2 hours, and a solution of 20 mL of concentrated hydrochloric acid/50 mL of water was added to the reaction solution. Stirring was performed at 25° C. for 0.5 hours. Then, a product was extracted with ethyl acetate (200 mL×2). The resulting organic layer was dried over anhydrous sodium sulfate and concentrated under reduced pressure to obtain 6.03 g of the title compound as a colorless oil (yield: 82%). $^1$H-NMR (400 MHz, CDCl$_3$) δ: 1.46 (d, 3H, J=6.3 Hz), 4.30 (s, 2H), 4.55 (q, 1H, J=6.3 Hz).

Example 2

(R)-1-Chloro-3-(tert-butyldimethylsilyloxy)butan-2-one

A mixture of 5.00 g (21.52 mmol) of ethyl (R)-2-(tert-butyldimethylsilyloxy)propionate, 3.76 g (32.3 mmol) of sodium chloroacetate, 2.18 g (21.5 mmol) of triethylamine, and 50 mL of THF was cooled in ice, and 37 mL (64.6 mmol) of a 1.75 M solution of tert-butylmagnesium chloride was added dropwise thereto over a period of 1 hour. After the completion of the dropwise addition, the reaction was allowed to proceed at 0° C. for 3 hours, and 6 M hydrochloric acid (about 20 mL) was added to the reaction solution to adjust the pH to 6.0. Subsequently, stirring was performed at 25° C. for 2 hours. A product was extracted with ethyl acetate (100 mL×2). The resulting organic layer was dried over anhydrous sodium sulfate and concentrated under reduced pressure to obtain 5.19 g of the title compound as a colorless oil (yield: 100%). $^1$H-NMR (400 MHz, CDCl$_3$) δ: 0.10 (S, 6H), 0.92 (s, 9H), 1.24 (d, 3H, J=6.8 Hz), 4.35 (q, 1H, J=6.8 Hz), 5.50 (q, 2H, J=17.0 Hz).

Example 3

1-Chloro-2-(2,4-difluorophenyl)-3-(tert-butyldimethylsilyloxy)butan-2-ol

Under a nitrogen atmosphere, 0.693 g (28.5 mmol) of magnesium was immersed in 5 mL of anhydrous THF, and a solution of 5.00 g (26.0 mmol) of 2,4-difluorophenylbromobenzene in 21 mL of THF was added dropwise thereto at 0° C. After the completion of the dropwise addition, stirring was performed at 0° C. for 2 hours and then at room temperature for another 1 hour to obtain 2,4-difluorophenylmagnesium bromide (0.62 M).

Next, a solution of 0.69 g (3.0 mmol) of (R)-1-chloro-3-(tert-butyldimethylsilyloxy)butan-2-one in 5 mL of THF was cooled to 0° C., and 5.3 mL (3.3 mmol) of 2,4-difluorophenylmagnesium bromide prepared as described above was added dropwise thereto over a period of 15 minutes. After the completion of the dropwise addition, stirring was continued for another 2 hours, and then 10 mL of a saturated aqueous solution of ammonium chloride was added to stop the reaction. Furthermore, 10 mL of water was added thereto, and extraction was performed with ethyl acetate (20 mL×2). After drying over anhydrous sodium sulfate, concentration was performed under reduced pressure to obtain 1.01 g of a colorless oil. A quantitative analysis was performed by HPLC (column: COSMOSIL manufactured by Nacalai Tesque Inc., mobile phase: acetonitrile/aqueous solution of 0.01 wt % phosphoric acid=7/3, flow rate: 1.0 mL/min, column temperature: 40° C., detector: UV 210 nm, retention time: 25 minutes (2S,3R), 20 minutes (2R,3R)). Thereby, 0.92 g of the title compound was obtained (yield: 89%) ((2S,3R): (2R,3R) =91:9). $^1$H-NMR (400 MHz, CDCl$_3$) (2S,3R) δ: 0.10 (s, 6H), 0.93 (s, 12H), 3.85 (d, 1H, J=12.0 Hz), 4.07 (d, 1H, J=12.0 Hz), 4.36 (q, 1H, J=6.6 Hz) 6.77-6.80 (m, 1H), 6.91-6.93 (m, 1H), 7.69-7.71 (m, 1H).

Example 4

1-Chloro-2-(2,4-difluorophenyl)-3-(tert-butyldimethylsilyloxy)butan-2-ol

A solution of 0.69 g (3.0 mmol) of (R)-1-chloro-3-(tert-butyldimethylsilyloxy)butan-2-one in 5 mL of THF was cooled to −20° C., and 5.3 mL (3.3 mmol) of a solution of 2,4-difluorophenylmagnesium bromide prepared by the same method as that in Example 3 was added dropwise over a period of 15 minutes. After the completion of the dropwise addition, stirring was continued for another 2 hours, and then 10 mL of a saturated aqueous solution of ammonium chloride was added to stop the reaction. Furthermore, 10 mL of water was added thereto, and extraction was performed with ethyl acetate (20 mL×2). After drying over anhydrous sodium sulfate, concentration was performed under reduced pressure to obtain a colorless oil. A quantitative analysis was performed by HPLC (under the same HPLC measurement conditions as those in Example 3). Thereby, the title compound was obtained in a yield of 68% ((2S,3R):(2R,3R)=92:8).

Example 5

1-Chloro-2-(2,4-difluorophenyl)-3-(tert-butyldimethylsilyloxy)butan-2-ol

A solution of 0.69 g (3.0 mmol) of (R)-1-chloro-3-(tert-butyldimethylsilyloxy)butan-2-one in 5 mL of toluene was cooled to 0° C., and 5.3 mL (3.3 mmol) of a solution of 2,4-difluorophenylmagnesium bromide prepared by the same method as that in Example 3 was added dropwise over a period of 15 minutes. After the completion of the dropwise addition, stirring was continued for another 2 hours, and then 10 mL of a saturated aqueous solution of ammonium chloride was added to stop the reaction. Furthermore, 10 mL of water was added thereto, and extraction was performed with ethyl acetate (20 mL×2). After drying over anhydrous sodium sulfate, concentration was performed under reduced pressure to obtain a colorless oil. A quantitative analysis was performed by HPLC (under the same HPLC measurement conditions as those in Example 3). Thereby, the title compound was obtained in a yield of 94% ((2S,3R): (2R,3R)=90:10).

Example 6

1-Chloro-2-(2,4-difluorophenyl)butane-2,3-diol

To a solution of 0.45 g (1.28 mmol) of 1-chloro-2-(2,4-difluorophenyl)-3-(tert-butyldimethylsilyloxy)butan-2-ol ((2S,3R)/(2R,3R)=91/9)) in 5 mL of methanol was added 0.25 mL of concentrated hydrochloric acid at room temperature. After the completion of the dropwise addition, stirring was performed at room temperature for 18 hours. Then, 10 mL of water was added to stop the reaction, and extraction was performed with 20 mL of ethyl acetate. The resulting organic layer was dried over anhydrous sodium sulfate and concentrated under reduced pressure to obtain a crude product as a colorless oil. A quantitative analysis was performed by HPLC. Thereby, the title compound was obtained in a yield of 77% ((2S,3R)/(2R,3R))=90/10) (HPLC, column: CAPCELL PAK C18 TYPE MG manufactured by Shiseido Co. Ltd., mobile phase: acetonitrile/20 mM (potassium) phosphate buffer solution (pH=2.5)=3/7, flow rate: 1.0 mL/min, column temperature: 30° C., detector: UV 210 nm, retention time: 26 minutes (2S,3R), 17 minutes (2R,3R). $^1$H-NMR (400 MHz, CDCl$_3$) (2S,3R) δ: 0.98 (d, 3H, J=6.6 Hz), 2.50 (brs, 1H), 3.21 (s, 1H), 4.11-4.23 (m, 3H), 6.77-6.80 (m, 1H), 6.91-6.93 (m, 1H), 7.69-7.71 (m, 1H); (2R,3R) δ: 1.93 (dd, 3H, J=6.3, 1.2 Hz), 2.25 (d, 1H, J=5.2 Hz), 3.15 (s, 1H), 3.96 (d, J=11.0 Hz), 4.08 (q, 1H, J=6.3 Hz), 4.35 (d, J=11.2 hz), 6.77-6.80 (m, 1H), 6.91-6.93 (m, 1H), 7.69-7.71 (m, 1H)).

Example 7

(2S,3R)-1-Chloro-2-(2,4-difluorophenyl)butane-2,3-diol

A solution of 0.45 g (1.28 mmol) of 1-chloro-2-(2,4-difluorophenyl)-3-(tert-butyldimethylsilyloxy)butan-2-ol ((2S,3R)/(2R,3R)=91/9) in 5 mL of THF was cooled in ice, and 1.3 mL of a 1.0 M solution of TBAF in THF was added dropwise. After the completion of the dropwise addition, reaction was performed for 1.5 hours and then at room temperature for another 11 hours. Next, 10 mL of water was added to stop the reaction, and extraction was performed with 20 mL of ethyl acetate. The resulting organic layer was dried over anhydrous sodium sulfate and concentrated under reduced pressure to obtain a crude product as a colorless oil. A quantitative analysis was performed by HPLC (under the same HPLC measurement conditions as those in Example 6). Thereby, the title compound was obtained in a yield of 15% ((2S,3R)/(2R,3R)=91/9).

Example 8

1-Chloro-2-(2,4-difluorophenyl)butane-2,3-diol

To a solution of 0.27 g (0.77 mmol) of 1-chloro-2-(2,4-difluorophenyl)-3-(tert-butyldimethylsilyloxy)butan-2-ol ((2S,3R)/(2R,3R)=91/9) in 3 mL of methanol was added 0.06 g (0.94 mmol) of potassium fluoride, and reaction was performed for 10 hours and then at 50° C. for another 25 hours. Next, 5 mL of water was added to stop the reaction, and extraction was performed with 10 mL of ethyl acetate. The resulting organic layer was dried over anhydrous sodium sulfate and concentrated under reduced pressure to obtain a crude product as a colorless oil. The resulting crude product was quantitatively analyzed by HPLC (under the same HPLC measurement conditions as those in Example 6). Thereby, the title compound was obtained in a yield of 17% ((2S,3R)/(2R,3R)=95/5).

Example 9

(2R,3R)-1,2-Epoxy-2-(2,4-difluorophenyl)butan-3-ol

A solution of 0.12 g (0.45 mmol) of (2S,3R)-1-chloro-2-(2,4-difluorophenyl)butane-2,3-diol in 3 mL of methanol was cooled in ice, and 0.12 g (0.6 mmol) of a 28% solution of NaOMe in methanol was added. Reaction was performed for 2 hours, and 10 mL of water was added to stop the reaction. Extraction was performed with ethylacetate (10 mL). After drying over anhydrous sodium sulfate, concentration was performed under reduced pressure to obtain a crude product. The resulting crude product was purified by column on silica gel to obtain 0.09 g of the title compound (yield: 96%).

Example 10

1,2-Epoxy-2-(2,4-difluorophenyl)butan-3-ol

A solution of 0.28 g (1.2 mmol) of (2S,3R)-1-chloro-2-(2,4-difluorophenyl)butane-2,3-diol ((2S,3R)/(2R,3R)=88/12) in 3 mL of methanol was cooled in ice, and 1.4 mL of a 1 M aqueous solution of NaOH was added thereto. Reaction was performed for 1.5 hours, and 10 mL of water was added to stop the reaction. Extraction was performed with ethylacetate (20 mL). After drying over anhydrous sodium sulfate, concentration was performed under reduced pressure to obtain a crude product. The resulting crude product was quantitatively analyzed by HPLC. Thereby, the title compound was obtained in a yield of 95% ((2R,3R)/(2S,3R)=88/12) (HPLC, column: CAPCELL PAK C18 TYPE MG, mobile phase: acetonitrile/20 mM (potassium) phosphate buffer solution (pH=2.5)=2/8, flow rate: 1.0 mL/min, column temperature: 30° C., detector: UV 210 nm, retention time: 28 minutes (2S,3R), 30 minutes (2R,3R)) $^1$H-NMR (400 MHz, CDCl$_3$) (2R,3R) δ: 1.16 (d, 3H, J=6.1 Hz), 2.80 (d, 1H, J=4.4 Hz), 3.30 (d, 1H, J=4.4 Hz), 4.09 (q, 1H, J=6.1 Hz), 6.80-6.93 (m, 2H), 7.32-7.37 (m, 1H)).

Example 11

(S)-1-Chloro-3-(tert-butyldimethylsilyloxy)butan-2-one

A mixture of 5.00 g (21.52 mmol) of ethyl (S)-2-(tert-butyldimethylsilyloxy)propionate, 3.76 g (32.3 mmol) of sodium chloroacetate, 2.18 g (21.5 mmol) of triethylamine, and 50 mL of THF was cooled in ice, and 37 mL (64.6 mmol) of a 1.75 M solution of tert-butylmagnesium chloride was added dropwise thereto over a period of 1 hour. After the completion of the dropwise addition, reaction was performed at 0° C. for another 3 hours, and 6 M hydrochloric acid (about 20 mL) was added to the reaction solution to adjust the pH to 6.0. Subsequently, stirring was performed at 25° C. for 2 hours. A product was extracted with ethyl acetate (100 mL×2). The resulting organic layer was dried over anhydrous sodium sulfate and concentrated under reduced pressure to obtain 5.01 g of the title compound as a colorless oil (yield: 98%). $^1$H-NMR (400 MHz, CDCl$_3$) δ: 0.10 (s, 6H), 0.92 (s, 9H), 1.24 (d, 3H, J=6.8 Hz), 4.35 (q, 1H, J=6.8 Hz), 5.50 (q, 2H, J=17.0 Hz).

Example 12

1-Chloro-2-(2,4-difluorophenyl)-3-(tert-butyldimethylsilyloxy)butan-2-ol

A solution of 0.69 g (3.0 mmol) of (S)-1-chloro-3-(tert-butyldimethylsilyloxy)butan-2-one in 5 mL of toluene was cooled to −20° C., and 5.3 mL (3.3 mmol) of a solution of 2,4-difluorophenylmagnesium bromide prepared by the same method as that in Example 3 was added dropwise thereto over a period of 15 minutes. After the completion of the dropwise addition, stirring was continued for another 2 hours, and 10 mL of a saturated aqueous solution of ammonium chloride was added to stop the reaction. Furthermore, 10 mL of water was added, and extraction was performed with ethyl acetate (20 mL×2). After drying over anhydrous sodium sulfate, concentration was performed under reduced pressure to obtain a colorless oil. A quantitative analysis was performed by HPLC (under the same HPLC measurement conditions as those in Example 3). Thereby, the title compound was obtained in a yield of 91% ((2R,3S)/(2S,3S)=92/8). $^1$H-NMR (400 MHz, CDCl$_3$) (2R,3S) δ: 0.10 (s, 6H), 0.92 (s, 12H), 3.85 (d, 1H, J=12.0 Hz), 4.07 (d, 1H, J=12.0 Hz), 4.35 (q, 1H, J=6.6 Hz), 6.77-6.79 (m, 1H), 6.93-6.93 (m, 1H), 7.69-7.71 (m, 1H).

Example 13

1-Chloro-2-(2,4-difluorophenyl)butane-2,3-diol

To a solution of 0.45 g (1.28 mmol) of 1-chloro-2-(2,4-difluorophenyl)-3-(tert-butyldimethylsilyloxy)butan-2-ol ((2R,3S)/(2S,3S)=92/8) in 5 mL of methanol was added 0.25 mL of concentrated hydrochloric acid at room temperature. After the completion of the dropwise addition, stirring was performed at room temperature for 18 hours. Then, 10 mL of water was added to stop the reaction, and extraction was performed with ethyl acetate (20 mL). The resulting organic layer was dried over anhydrous sodium sulfate and concentrated under reduced pressure to obtain a crude product as a colorless oil. A quantitative analysis was performed by HPLC (under the same HPLC measurement conditions as those in Example 6). Thereby, the title compound was obtained in a yield of 75% ((2R,3S)/(2S,3S)=91/9). $^1$H-NMR (400 MHz, CDCl$_3$) (2R,3S) δ: 0.98 (d, 3H, J=6.6 Hz), 2.48 (brs, 1H), 3.20 (s, 1H), 4.11-4.23 (m, 3H), 6.77-6.80 (m, 1H), 6.91-6.93 (m, 1H), 7.69-7.71 (m, 1H); (2S,3S) δ: 1.93 (dd, 3H, J=6.3, 1.2 Hz), 2.25 (d, 1H, J=5.2 Hz), 3.15 (s, 1H), 3.97 (d, J=11.0 Hz), 4.06 (q, 1H, J=6.3 Hz), 4.35 (d, J=11.2 Hz), 6.75-6.82 (m, 1H), 6.91-6.93 (m, 1H), 7.69-7.71 (m, 1H).

Example 14

(2S,3S)-1,2-Epoxy-2-(2,4-difluorophenyl)butan-3-ol

A solution of 0.12 g (0.45 mmol) of (2R,3S)-1-chloro-2-(2,4-difluorophenyl)butane-2,3-diol in methanol 3 mL was cooled in ice, and 0.12 g (0.6 mmol) of a 28% solution of NaOMe in methanol was added. Reaction was performed for 2 hours. Then, 10 mL of water was added to stop the reaction, and extraction was performed with ethyl acetate (10 mL). After drying over anhydrous sodium sulfate, concentration was performed under reduced pressure to obtain a crude product. The resulting crude product was purified by column on silica gel to obtain 0.086 g of the title compound (yield: 96%).

Example 15

(R)-1-Chloro-3-trimethylsilyloxybutan-2-one

A mixture of 5.00 g (42.3 mmol) of (R)-ethyl lactate, 7.40 g (63.5 mmol) of sodium chloroacetate, 4.28 g (42.3 mmol) of triethylamine, and 50 mL of THF was cooled in ice, and 97 g (109 mmol) of a 1.75 M solution of tert-butylmagnesium chloride was added dropwise thereto over a period of 2 hours. After the completion of the dropwise addition, the reaction was performed at room temperature for another 2 hours, and a solution of 20 mL of concentrated hydrochloric acid/50 mL of water was added to the reaction solution. Stirring was performed at 25° C. for 0.5 hours. Then, a product was extracted with ethyl acetate (200 mL×2). The resulting organic layer was dried over anhydrous sodium sulfate and concentrated under reduced pressure to obtain a colorless oil.

Next, the resulting concentrate was dissolved in 50 mL of THF, and 8.1 mL (63.5 mmol) of TMSCl was added dropwise thereto over a period of 5 minutes under ice cooling. Subsequently, 11.8 mL (84.6 mmol) of triethylamine was added dropwise at the same temperature over a period of 10 minutes. After the reaction was performed for another 1 hour, 80 mL of water was added, and extraction was performed with ethyl acetate (100 mL×2). Drying was performed with anhydrous sodium sulfate, and then concentration was performed under reduced pressure to obtain 5.04 g of the title compound as an oil (yield: 61%). $^1$H-NMR (400 MHz, CDCl$_3$) δ: 0.17 (s, 9H), 1.35 (d, 3H, J=6.0 Hz), 4.35 (q, 1H, J=6.0 Hz), 4.48 (d, 2H, J=17.1 Hz).

Example 16

1-Chloro-2-(2,4-difluorophenyl)-3-(trimethylsilyloxy)butan-2-ol

A solution of 0.7 g (3.6 mmol) of (R)-1-chloro-3-(trimethylsilyloxy)butan-2-one in 5 mL of THF was cooled to 0° C., 5.4 mL (3.8 mmol) of a 0.7 M solution of 2,4-difluorophenylmagnesium bromide prepared by the same method as that in Example 3 was added dropwise thereto over a period of 10 minutes. After the completion of the dropwise addition, stirring was continued for another 5 hours, and 10 mL of a saturated aqueous solution of ammonium chloride was added to stop the reaction. Furthermore, 10 mL of water was added, and extraction was performed with ethyl acetate (20 mL×2). After drying over anhydrous sodium sulfate, concentration was performed under reduced pressure to obtain 1-chloro-2-(2,4-difluorophenyl)butane-2,3-diol. A quantitative analysis was performed by HPLC (under the same HPLC measurement conditions as those in Example 6). As a result, the yield was determined to be 87% ((2S,3R)/(2R,3R)=41/59).

Example 17

1-Chloro-2-(2,4-difluorophenyl)-3-(trimethylsilyloxy)butan-2-ol

A solution of 0.7 g (3.6 mmol) of (R)-1-chloro-3-(trimethylsilyloxy)butan-2-one in 5 mL of THF was cooled to −20° C., and 5.4 mL (3.8 mmol) of a 0.7 M solution of 2,4-difluorophenylmagnesium bromide prepared by a method as that in Example 3 was added dropwise thereto over a period of 10 minutes. After the completion of the dropwise addition, stirring was continued for another 5 hours, and 10 mL of a saturated aqueous solution of ammonium chloride was added to stop the reaction. Furthermore, 10 mL of water was added, and extraction was performed with ethyl acetate (20 mL×2). After drying over anhydrous sodium sulfate, concentration was performed under reduced pressure to obtain 1-chloro-2-(2,4-difluorophenyl)butane-2,3-diol as a colorless oil. A quantitative analysis was performed by HPLC (under the same HPLC measurement conditions as those in Example 6). As a result, the yield was determined to be 79% ((2S,3R)/(2R,3R)=43/57).

Example 18

(R)-1-Chloro-3-pivaloyloxybutan-2-one

A mixture of 32.8 g (147 mmol) of methyl (R)-2-pivaloyloxypropionate, 30.5 g (261.8 mmol) of sodium chloroacetate, 26.4 g (261.55 mmol) of triethylamine, and 400 mL of THF was cooled in ice, and 299 g (523.5 mmol) of a 1.75 M solution of tert-butylmagnesium chloride was added dropwise thereto over a period of 3 hours. After the completion of the dropwise addition, the reaction was performed at 25° C. for another 2 hours, and the reaction solution was cooled in ice. A solution of 45 ml of concentrated hydrochloric acid/200 ml of water was added thereto, and subsequently 250 mL of ethyl acetate was added. Furthermore, concentrated hydrochloric acid was added for adjusting the pH to 6.0. Stirring was performed at 25° C. for 1 hour. The resulting ethyl acetate layer was separated, and 150 mL of ethyl acetate was added to the resulting aqueous layer to perform extraction again. The resulting ethyl acetate layers were combined, dried over anhydrous sodium sulfate, and concentrated under reduced pressure to obtain 42.6 g of a crude product as an oil. A quantitative analysis was performed by HPLC. Thereby, 29.4 g of the title compound was obtained (yield: 82%, 98.7% e.e.) (HPLC, column: YMC-A302 manufactured by YMC Co. Ltd.; mobile phase: acetonitrile/20 mM (potassium) phosphate buffer solution (pH=2.5)=6/4, flow rate: 1.0 mL/min, column temperature: 30° C., detector: UV 210 nm, retention time: 5 minutes) $^1$H-NMR (400 MHz, CDCl$_3$) δ: 1.25 (s, 9H), 1.46 (d, 1H, J=6.6 Hz), 4.30 (s, 2H), 5.27 (q, 1H, J=6.6 Hz).

Example 19

1-Chloro-2-(2,4-difluorophenyl)-3-pivaloyloxybutan-2-ol

A solution of 0.41 g (2.0 mmol) of (R)-1-chloro-3-pivaloyloxybutan-2-one in 5 mL of THF was cooled to 0° C., and 3.2 mL (2.2 mmol) of a 0.69 M solution of 2,4-difluorophenylmagnesium bromide prepared by the same method as that in Example 3 was added dropwise thereto over a period of 5 minutes. After the completion of the dropwise addition, stirring was continued for another 1 hour, and 10 mL of a saturated aqueous solution of ammonium chloride was added to stop the reaction. Furthermore, 10 mL of water was added, and extraction was performed with ethyl acetate (20 mL×2). After drying over anhydrous sodium sulfate, concentration was performed under reduced pressure to obtain a crude product. A quantitative analysis was performed by HPLC. Thereby, the title compound was obtained in a yield of 15% ((2S,3R)/(2R,3R)=92/8) (HPLC, column: YMC-A302 manufactured by YMC Co. Ltd., mobile phase: acetonitrile/20 mM (potassium) phosphate buffer solution (pH=2.5)=6/4, flow rate: 1.0 mL/min, column temperature: 30° C., detector: UV 210 nm, retention time: 10 minutes (2S,3R) and 8 minutes (2R,3R)). $^1$H-NMR (400 MHz, CDCl$_3$) δ: 1.05 (d, 3H, J=6.3 Hz), 1.25 (s, 9H), 3.86 (d, 1H, J=11.5 Hz), 4.19 (d, 1H, 11.5 Hz), 5.38 (q, 1H, J=6.3 Hz), 6.77-6.80 (m, 1H), 6.91-6.93 (m, 1H), 7.69-7.71 (m, 1H).

Example 20

1-Chloro-2-(2,4-difluorophenyl)-3-pivaloyloxybutan-2-ol

A solution of 0.41 g (2.0 mmol) of (R)-1-chloro-3-pivaloyloxybutan-2-one in 5 mL of toluene was cooled to 0° C., and 3.2 mL (2.2 mmol) of a 0.69 M solution of 2,4-difluorophenylmagnesium bromide prepared by the same method as that in Example 3 was added dropwise thereto over a period of 5 minutes. After the completion of the dropwise addition, stirring was continued for another 1 hour, and 10 mL of a saturated aqueous solution of ammonium chloride was added to stop the reaction. Furthermore, 10 mL of water was added, and extraction was performed with ethyl acetate (20 mL×2). After drying over anhydrous sodium sulfate, concentration was performed under reduced pressure to obtain 0.54 g of a crude product. The resulting product was purified by column on silica gel to obtain 0.450 g of the title compound (yield: 71%) ((2S,3R)/(2R,3R)=93/7 (the diastereomeric ratio was measured by HPLC under the same HPLC measurement conditions as those in Example 19)).

Example 21

1-Chloro-2-(2,4-difluorophenyl)-3-pivaloyloxybutan-2-ol

First, 8.9 mL (8.0 mmol) of a 0.9 M solution of 2,4-difluorophenylmagnesium bromide prepared by the same method as that in Example 3 was cooled to 0° C., and a solution of 0.83 g (4.0 mmol) of (R)-1-chloro-3-pivaloyloxybutan-2-one in 10 mL of toluene was added dropwise thereto over a period of 5 minutes. After the completion of the dropwise addition, stirring was continued for another 1 hour, and 20 mL of a saturated aqueous solution of ammonium chloride was added to stop the reaction. Furthermore, 10 mL of water was added, and extraction was performed with ethyl acetate (30 mL×2). After drying over anhydrous sodium sulfate, concentration was performed under reduced pressure to obtain 1.57 g of a crude product. A quantitative analysis was performed by HPLC. Thereby, the title compound was obtained in a yield of 94% ((2S,3R)/(2R,3R)=93/7 (the diastereomeric ratio was measured by HPLC under the same HPLC measurement conditions as those in Example 19)).

Example 22

1-Chloro-2-(2,4-difluorophenyl)-3-pivaloyloxybutan-2-ol

A solution of 0.41 g (2.0 mmol) of (R)-1-chloro-3-pivaloyloxybutan-2-one in 5 mL of toluene was cooled to −20° C., and 3.2 mL (2.2 mmol) of a 0.69 M solution of 2,4-difluorophenylmagnesium bromide prepared by the same method as that in Example 3 was added dropwise thereto over a period of 5 minutes. After the completion of the dropwise addition, stirring was continued for another 1 hour, and 10 mL of a saturated aqueous solution of ammonium chloride was added to stop the reaction. Furthermore, 10 mL of water was added, and extraction was performed with ethyl acetate (20 mL×2). After drying over anhydrous sodium sulfate, concentration was performed under reduced pressure to obtain a crude product. A quantitative analysis was performed by HPLC. Thereby, the title compound was obtained in a yield of 60% ((2S,3R)/(2R,3R)=94/6 (the diastereomeric ratio was measured by HPLC under the same HPLC measurement conditions as those in Example 19)).

Example 23

1,2-Epoxy-2-(2,4-difluorophenyl)butan-3-ol

A solution of 0.45 g (1.4 mmol) of 1-chloro-2-(2,4-difluorophenyl)-3-(pivaloyloxy)butan-2-ol ((2S,3R)/(2R,3R)=93/7)) in 3 mL of methanol was cooled to 0° C., and 0.33 g (1.7 mmol) of a 28% solution of NaOMe in methanol was added. The reaction was performed for 1 hour and at room temperature for another 16 hours. Then, 5 mL of water was added to stop the reaction, and extraction was performed with ethyl acetate (20 mL). After drying over anhydrous sodium sulfate, concentration was performed under reduced pressure to obtain 0.31 g of a crude product. The resulting product was purified by column on silica gel to obtain 0.11 g of the title compound (yield: 40%) ((2R,3R)/(2S,3R)=96/4 (the diastereomeric ratio was measured by HPLC under the same HPLC measurement conditions as those in Example 10)).

Example 24

(R)-1-Chloro-3-(3,4,5,6-tetrahydro-2H-pyran-2-yloxy)butan-2-one

A mixture of 9.41 g (50 mmol) of methyl (R)-2-(3,4,5,6-tetrahydro-2H-pyran-2-yloxy)propionate, 8.74 g (75 mmol) of sodium chloroacetate, 7.53 g (75 mmol) of triethylamine, and 200 mL of THF was cooled in ice, and 199 g (300 mmol) of a 1.6 M solution of tert-butylmagnesium chloride was added dropwise thereto over a period of 2 hours. After the completion of the dropwise addition, the reaction was performed at room temperature for another 2 hours, and the reaction solution was cooled in ice again. Then, 50 mL of water was added thereto, and subsequently 100 mL of ethyl acetate was added. Furthermore, 10% hydrochloric acid was added in such a manner that the pH was 6.0. After stirring was performed at room temperature for 1 hour, the resulting organic layer was separated, dried over anhydrous sodium sulfate, and concentrated under reduced pressure to obtain 9.81 g of a crude product. The resulting product was purified by column on silica gel to obtain 6.79 g of the title compound (yield: 73%). $^1$H-NMR (400 MHz, CDCl$_3$) δ: 1.35 (d, 3H, J=6.6 Hz), 1.50-1.55 (m, 4H), 1.80-1.84 (m, 3H), 3.42-3.53 (m, 1H), 3.83-3.96 (m, 1H), 4.24 (q, 1H, J=6.8 Hz), 5.58 (m, 2H).

Example 25

1-Chloro-2-(2,4-difluorophenyl)-3-(3,4,5,6-tetrahydro-2H-pyran-2-yloxy)butan-2-ol A solution of 0.413 g (2.0 mmol) of (R)-1-chloro-3-(3,4,5,6-tetrahydro-2H-pyran-2-yloxy)butan-2-one in 5 mL of THF was cooled to 0° C., and 2.7 mL (2.2 mmol) of a 0.81M solution of 2,4-difluorophenylmagnesium bromide prepared by the same method as that in Example 3 was added dropwise thereto over a period of 5 minutes. After the completion of the dropwise addition, stirring was continued for another 2 hours, and 10 mL of a saturated aqueous solution of ammonium chloride was added to stop the reaction. Furthermore, 10 mL of water was added, and extraction was performed with ethyl acetate (20 mL×2). After drying over anhydrous sodium sulfate, concentration was performed under reduced pressure to obtain 0.634 g of colorless oil. The resulting oil was purified by column on silica gel to obtain 0.51 g of the title compound (yield: 79%) ((2R,3R)/(2S,3R)=82/18 (the diastereomeric ratio was measured by HPLC; HPLC conditions, column: YMC-A302 manufactured by YMC Co. Ltd., mobile phase: acetonitrile/20 mM (potassium) phosphate buffer solution (pH=2.5)=6/4, flow rate: 1.0 mL/min, column temperature: 30° C., detector: UV 210 nm, retention time: 15 and 17 minutes (2R,3R) 19 and 22 minutes (2S,3R))). $^1$H-NMR (400 MHz, CDCl$_3$) (2R,3R) δ: 0.87-1.86 (m, 10H), 3.43-3.45 (m, 1H), 3.81-4.39 (m, 4H), 6.77-6.80 (m, 1H), 6.91-6.93 (m, 1H), 7.69-7.71 (m, 1H); (2S,3R) δ: 0.95-1.85 (m, 10H), 3.42-3.55 (m, 1H), 3.85-4.95 (m, 4H), 6.77-6.80 (m, 1H), 6.91-6.93 (m, 1H), 7.69-7.71 (m, 1H).

Example 26

(2R,3R)-1-Chloro-2-(2,4-difluorophenyl)butane-2,3-diol

A mixed solution of 0.15 g (0.47 mmol) of (2R,3R)-1-chloro-2-(2,4-difluorophenyl)-3-(3,4,5,6-tetrahydro-2H-pyran-2-yloxy)butan-2-ol, 5 mL of methanol, and 0.02 g of p-toluenesulfonic acid monohydrate was stirred at room temperature for 30 minutes. Concentration was performed under reduced pressure to obtain a crude product. The resulting product was purified by column on silica gel to obtain 0.12 g of the title compound (yield: 97%).

Example 27

(2S,3R)-1,2-Epoxy-2-(2,4-difluorophenyl)butan-3-ol

A solution of 1.00 g (4.23 mmol) of (2R,3R)-1-chloro-2-(2,4-difluorophenyl)butane-2,3-diol in 8 mL of methanol was cooled in ice, and 0.91 g (4.65 mmol) of a 28% solution of NaOMe in methanol was added thereto. The reaction was performed for 2 hours, and 10 mL of water was added to stop the reaction. Then, extraction was performed with 20 mL of ethyl acetate. After drying over anhydrous sodium sulfate, concentration was performed under reduced pressure to obtain a crude product. The product was quantitatively analyzed by HPLC (under the same HPLC measurement conditions as those in Example 10). The title compound was obtained in a yield of 97%. $^1$H-NMR (400 MHz, CDCl$_3$) δ: 1.19 (d, 3H, J=6.3 Hz), 2.22 (s, 1H), 2.91 (d, 1H, J=4.9 Hz), 3.28 (d, 1H, J=4.9 Hz), 4.11 (d, 1H, J=6.3 Hz), 6.80-6.91 (m, 2H), 7.34-7.39 (m, 1H).

Example 28

(R)-1-Chloro-3-(tert-butyloxy)butan-2-one

A mixture of 8.00 g (50 mmol) of methyl (R)-2-(tert-butyloxy)propionate, 8.74 g (75 mmol) of sodium chloroacetate, 7.53 g (75 mmol) of triethylamine, and 200 mL of THF was cooled in ice, and 93.8 g (150 mmol) of a 1.6 M solution of tert-butylmagnesium chloride was added dropwise thereto over a period of 2 hours. After the completion of the dropwise addition, the reaction was performed at room temperature for another 2 hours, the reaction solution was cooled in ice again. Then, 20 mL of concentrated hydrochloric acid was added thereto, and subsequently 100 mL of ethyl acetate was added. Stirring was performed at room temperature for 1 hour. Then, the resulting organic layer was separated, dried over anhydrous sodium sulfate, and concentrated under reduced pressure to obtain 7.35 g of a crude product. The resulting product was purified by column on silica gel to obtain 6.66 g of the title compound (yield: 80%). $^1$H-NMR (400 MHz, CDCl$_3$) δ: 1.21 (s, 9H), 1.35 (d, 3H, J=6.6 Hz), 4.20 (q, 1H, J=6.6 Hz), 5.50 (s, 2H).

Example 29

1-Chloro-2-(2,5-difluorophenyl)-3-pivaloyloxybutan-2-ol

A solution of 2,5-difluorophenylmagnesium bromide prepared from 5.79 g (30.0 mmol) of 2,5-difluorobromobenzene and 0.759 g (31.2 mmol) of magnesium by the same method as that in Example 3 was cooled to 0° C., and a solution of 3.10 g (15.0 mmol) of (R)-1-chloro-3-pivaloyloxybutan-2-one in 15 mL of toluene was added dropwise thereto. After the completion of the dropwise addition, stirring was continued for another 1 hour, and 10 mL of a saturated aqueous solution of ammonium chloride was added to stop the reaction. Furthermore, 10 mL of water was added, and extraction was performed with ethyl acetate (20 mL×2). After drying over anhydrous sodium sulfate, concentration was performed under reduced pressure to obtain a crude product. A quantitative analysis was performed by HPLC. Thereby, the title compound was obtained in a yield of 63% ((2S,3R)/(2R,3R)=94/6) (HPLC, column: YMC-A302 manufactured by YMC Co. Ltd., mobile phase: acetonitrile/20 mM (potassium) phosphate buffer solution (pH=2.5)=6/4, flow rate: 1.0 mL/min, column temperature: 30° C., detector: UV 210 nm, retention time: 17.0 minutes (2S,3R), 13 minutes (2R,3R)). $^1$H-NMR (400 MHz, CDCl$_3$) (2S,3R) δ: 1.07 (d, 3H, J=6.3 Hz), 1.24 (s, 9H), 3.86 (d, 1H, J=11.5 Hz), 4.20 (d, 1H, 11.5 Hz), 5.42 (q, 1H, J=6.3 Hz), 7.00-7.03 (m, 2H), 7.40-7.44 (m, 1H); (2R,3R) δ: 1.03 (s, 9H), 1.58 (d, 3H, J=6.3 Hz), 3.91 (d, 1H, J=11.5 Hz), 4.28 (d, 1H, 11.5 Hz), 5.31 (q, 1H, J=6.3 Hz), 6.99-7.02 (m, 2H), 7.26-7.37 (m, 1H).

Example 30

1,2-Epoxy-2-(2,5-difluorophenyl)butan-3-ol

A solution of 1.70 g (5.3 mmol) of 1-chloro-2-(2,5-difluorophenyl)-3-(pivaloyloxy)butan-2-ol ((2S,3R)/(2R,3R)=94/6) in 20 mL of THF was cooled to 0° C., and 3.5 g (17.8 mmol) of a 28% solution of NaOMe in methanol was added thereto. The reaction was performed for 5 hours, and 20 mL of 1 M hydrochloric acid was added to stop the reaction. Then, extraction was performed with ethylacetate (30 mL). After drying over anhydrous sodium sulfate, concentration was performed under reduced pressure to obtain 1.51 g of a crude product. The resulting product was purified by column on silica gel to obtain 0.838 g of the title compound (yield: 79%) ((2R,3R)/(2S,3R)=98/2 (the diastereomeric ratio was measured by HPLC under the same HPLC measurement conditions as those in Example 10, (2R,3R) 32 minutes, (2S,3R) 30 minutes). $^1$H-NMR (400 MHz, CDCl$_3$) (2R,3R) δ: 1.70 (d, 3H, J=6.6 Hz), 2.80 (d, 1H, J=5.1 Hz), 3.34 (d, 1H, J=5.1 Hz), 4.17 (q, 1H, 6.6 Hz), 6.98-7.00 (m, 2H), 7.14-7.26 (m, 1H)

Example 31

1-Chloro-2-(2,4-difluorophenyl)-3-(tert-butyloxy)butan-2-ol

A solution of 0.385 g (2.0 mmol) of (R)-1-chloro-3-(tert-butyloxy)butan-2-one in 5 mL of THF was cooled to 0° C., and 3.3 mL (2.2 mmol) of a 0.68 M solution of 2,4-difluorophenylmagnesium bromide prepared by the same method as that in Example 3 was added dropwise thereto over a period of 5 minutes. After the completion of the dropwise addition, stirring was continued for another 1 hour, and 10 mL of a saturated aqueous solution of ammonium chloride was added to stop the reaction. Furthermore, 10 mL of water was added, and extraction was performed with ethyl acetate (20 mL×2). After drying over anhydrous sodium sulfate, and concentration was performed under reduced pressure to obtain 0.489 g of an oil. The resulting oil was purified by column on silica gel to obtain 0.34 g of the title compound (yield: 58%) ((2S,3R)/(2R,3R)=59/41) (the diastereomeric ratio was measured by HPLC; HPLC conditions, column: YMC-A302 manufactured by YMC Co. Ltd., mobile phase: acetonitrile/20 mM (potassium) phosphate buffer solution (pH=2.5)=6/4, flow rate: 1.0 mL/min, column temperature: 30° C., detector: UV 210 nm, retention time: 8 minutes (2R,3R), 9 minutes (2S,3R)). $^1$H-NMR (400 MHz, CDCl$_3$) δ: 1.15-1.48 (m, 12H), 3.55-4.31 (m, 3H), 6.77-6.80 (m, 1H), 6.91-6.93 (m, 1H), 7.69-7.71 (m, 1H)

Example 32

(2R,3S)-2-(2,4-Difluorophenyl)-3-methyl-2-[(1H-1,2,4-triazol-1-yl)methyl]oxirane First, 0.21 g (5.10 mmol) of sodium hydride (60% content) was suspended in 3 mL of DMF, and the resulting suspension was cooled in ice. A solution of 0.53 g (2.19 mmol) of (2R,3R)-1-chloro-2-(2,4-difluorophenyl)butane-2,3-diol in 5 mL of DMF was added thereto, and stirring was performed for 1 hour. A solution of 0.64 g (2.85 mmol) of 1-(p-toluenesulfonyl)-1,2,4-triazole and 0.06 g (0.88 mmol) of triazole in 3 mL of DMF was added, and the reaction solution was stirred at 60° C. for 3 hours. Then, the reaction solution was cooled to room temperature, and 10 mL of water was added to stop the reaction. The resulting product was extracted with ethyl acetate (20 mL×2), and concentration was performed under reduced pressure. A quantitative analysis was performed by HPLC. Thereby, the title compound was obtained in a yield of 43% (HPLC conditions, column: CAPCELL PAK C18 TYPE MG manufactured by Shiseido Co. Ltd., mobile phase: acetonitrile/20 mM (potassium) phosphate buffer solution (pH=2.5)=2/8, flow rate: 1.0 mL/min, column temperature: 30° C., detector: UV 210 nm, retention time: 37 minutes). $^1$H-NMR (400 MHz, CDCl$_3$) δ: 1.64 (d, 3H, J=5.6 Hz), 3.19 (q, 1H, J=5.6 Hz), 4.42 (d, 1H, J=14.6 Hz), 4.87 (d, 1H, J=14.6 Hz), 6.69-6.80 (m, 2H), 6.98-7.03 (m, 1H), 7.81 (s, 1H), 7.98 (s, 1H).

Example 33

3,4-Epoxy-3-(2,5-difluorophenyl)-2-methylbutan-1-ol

A solution of 0.66 g (3.0 mmol) of (S)-1-chloro-3-methyl-4-pivaloyloxybutan-2-one in 4 mL of THF was cooled to 0° C., and 3.9 mL (3.3 mmol) of a 0.86 M solution of 2,5-difluorophenylmagnesium bromide prepared by the same method as that in Example 3 was added dropwise thereto over a period of 5 minutes. After the completion of the dropwise addition, stirring was continued for another 1 hour, 10 mL of a saturated aqueous solution of ammonium chloride was added to stop the reaction. Furthermore, 10 mL of water was added, and extraction was performed with ethyl acetate (20 mL×2). After drying over anhydrous sodium sulfate, concentration was performed under reduced pressure to obtain a crude product. The resulting product was purified by column on silica gel to obtain 0.50 g of 1-chloro-2-(2,5-difluorophenyl)-3-methyl-4-pivaloyloxybutan-2-ol as a diastereomeric mixture (yield: 50%) ((2S,3S):(2R,3S)=72:28) (HPLC, column: YMC-A302 manufactured by YMC Co. Ltd., mobile phase: acetonitrile/20 mM (potassium) phosphate buffer solution (pH=2.5)=6/4, flow rate: 1.0 mL/min, column temperature: 30° C., detector: UV 210 nm, retention time: 18 minutes (2S,3S), 20 minutes (2R,3S)). The resulting compound was dissolved in 10 mL of THF, and 1.02 g (5.25 mmol) of a 28% solution of NaOMe in methanol was added thereto under ice cooling. The reaction was performed for 5 hours. A reaction product was extracted with ethyl acetate (10 mL×2). After drying over anhydrous sodium sulfate, concentration was performed under reduced pressure to obtain a crude product. The resulting product was purified by column on silica gel to obtain 0.28 g of the title compound (yield: 88%) (HPLC, column: YMC-A302 manufactured by YMC Co. Ltd., mobile phase: acetonitrile/20 mM (potassium) phosphate buffer solution (pH=2.5)=3/7, flow rate: 1.0 mL/min, column temperature: 30° C., detector: UV 210 nm, retention time: 17 minutes (2R,3S), 18 minutes (2S,3S)). $^1$H-NMR (400 MHz, CDCl$_3$) (2R,3S) δ: 0.97 (d, 3H, J=6.6 Hz), 2.25 (q, 1H, J=6.6 Hz), 2.88 (d, 1H, J=4.4 Hz), 3.21 (d, 1H, J=4.4 Hz), 3.51 (d, 2H, J=6.1 Hz), 6.99-7.01 (m, 2H), 7.13-7.17 (m, 1H); (2S,3S) δ: 1.27 (d, 3H, J=6.6 Hz), 2.14 (q, 1H, J=6.6 Hz), 2.83 (d, 2H, J=4.4 Hz), 3.17 (d, 1H, J=4.4 Hz), 3.60 (d, 2H, J=5.9 Hz), 6.99-7.01 (m, 2H), 7.13-7.17 (m, 1H).

Example 34

3-(2,5-Difluorophenyl)-2-methyl-4-[1-(1,2,4-triazolyl)]-1,3-butanediol

The reaction of 0.44 g (2.1 mmol) of 3,4-epoxy-3-(2,5-difluorophenyl)-2-methylbutan-1-ol ((2S,3S): (2R,3S)=72:28), 0.21 g (3.0 mmol) of 1,2,4-triazole, 0.83 g (6.0 mmol) of potassium carbonate, and 10 mL of DMSO was performed at 80° C. for 2 hours. A reaction product was extracted with ethyl acetate (10 mL×2). After drying over anhydrous sodium sulfate, concentration was performed under reduced pressure to obtain a crude product. The resulting product was purified by column on silica gel to obtain 0.49 g of the title compound (yield: 83%) ((2S,3S)/(2R,3S)=70/30) (HPLC, column: YMC-A302 manufactured by YMC Co. Ltd., mobile phase: acetonitrile/20 mM (potassium) phosphate buffer solution (pH=2.5)=3/7, flow rate: 1.0 mL/min, column temperature: 30° C., detector: UV 210 nm, retention time: 6 minutes (2S, 3S), 8 minutes (2R,3S)). $^1$H-NMR (400 MHz, CDCl$_3$) (2S, 3S) δ: 1.36 (d, 3H, J=6.8 Hz), 2.36-2.42 (m, 2H), 3.48-3.57 (m, 2H), 4.56 (d, 1H, J=13.9 Hz), 4.87 (d, 2H, J=13.9 Hz), 5.19 (s, 1H), 6.85-6.97 (m, 2H), 7.12-7.17 (m, 1H), 7.26 (s, 1H), 7.90 (s, 1H); (2R,3S) δ: 0.86 (d, 3H, J=7.1 Hz), 2.35-2.37 (m, 1H), 3.51-3.54 (1H, brs), 3.84 (t, 1H, J=5.6 Hz), 4.0 (d, 1H, J=11.2 Hz), 4.77 (d, 1H, J=14.1 Hz), 4.98 (d, 1H, J=2.14 (q, 1H, J=6.6 Hz), 5.37 (s, 1H), 6.85-6.97 (m, 2H), 7.12-7.17 (m, 1H), 7.26 (s, 1H), 7.90 (s, 1H).

Production Example 1

(2R,3S)-2-(2,4-Difluorophenyl)-3-methyl-2-[(1H-1,2,4-triazol-1-yl)methyl]oxirane A solution of 0.25 g (1.25 mmol) of (2R,3R)-1,2-epoxy-2-(2,4-difluorophenyl)butan-3-ol ((2R,3R)/(2S,3R)=90/10)/ 0.19 mL (1.37 mmol) of triethylamine/2.5 mL of methylene chloride was cooled in ice, and 0.11 mL (1.37 mmol) of methanesulfonyl chloride was added thereto. The reaction was performed for 2 hours, and 10 mL of a saturated aqueous solution of sodium hydrogencarbonate was added to stop the reaction. Extraction was performed with ethyl acetate (20 mL×2). After drying over anhydrous sodium sulfate, concentration was performed under reduced pressure to obtain 0.35 g of an oil.

Next, 0.13 g (3.55 mmol) of sodium hydride (60% content) was suspended in 1 mL of DMF, and the resulting suspension was cooled in ice. Then, a solution of 0.29 g (4.15 mmol) of triazole in 3 mL of DMF was added thereto, and the reaction was performed for 1.5 hours. A solution of 0.35 g of the above-described oil in 3 mL of DMF was added thereto, and the reaction was performed at room temperature for 2 hours and then at 50° C. for 3.5 hours. Then, 5 mL of a saturated aqueous solution of ammonium chloride was added to stop the reaction, and extraction was performed with 30 mL of toluene. After drying over anhydrous sodium sulfate, concentration was performed under reduced pressure to obtain 0.284 g of yellow crystals. The resulting product was purified by column on silica gel to obtain 0.189 g of the title compound as white crystals (yield: 63%) ((2R,3S)/(2S,3S)=90/10 (the diastereomeric ratio was measured by HPLC; HPLC conditions, column: CAPCELL PAK C18 TYPE MG manufactured by Shiseido Co. Ltd., mobile phase: acetonitrile/20 mM (potassium) phosphate buffer solution (pH=2.5)=2/8, flow rate: 1.0 mL/min, column temperature: 30° C., detector: UV 210 nm, retention time: 37 minutes (2R,3S), 41 minutes (2S, 3S))).

Next, 0.170 g of the white crystals was suspended in 2 mL of hexane, and ethyl acetate was gradually added until the crystals were completely dissolved at 50° C. The resulting solution was left to cool to room temperature, and stirring was continued for 3 hours. Precipitated white crystals were filtrated to obtain the (2R,3S) diastereomer (0.07 g).

Production Example 2

(2R,3S)-2-(2,4-difluorophenyl)-3-methyl-2-[(1H-1,2,4-triazol-1-yl)methyl]oxirane A solution of 18.0 g (90.0 mmol) of (2R,3R)-1,2-epoxy-2-(2,4-difluorophenyl)butan-3-ol ((2R,3R)/(2S,3R)=93/7)/ 10.9 g (108 mmol) of triethylamine/150 mL of toluene was cooled in ice, and 12.4 g (108 mmol) of methanesulfonyl chloride was added. The reaction was performed for 2 hours. Then, 30 mL of water was added, and subsequently 50 mL of 5% aqueous solution of potassium hydroxide was added to stop the reaction. The organic phase was separated, dried over anhydrous sodium sulfate, and concentrated under reduced pressure to obtain 32.07 g of an oil.

A mixture of 4.2 g (21.6 mmol) of a 28% solution of NaOMe in methanol, 1.5 g (21.6 mmol) of triazole, and 16 mL of DMF was stirred at room temperature for 1 hour, and a solution of 5.0 g (18.0 mmol) of the above-described mesylate in 19 mL of DMF was added thereto at a time. The reaction was performed at 60° C. for 7 hours. The resulting reaction solution was cooled to 0° C., and 90 mL of water was added dropwise to stop the reaction. Then, 90 mL of toluene was added. The organic phase was separated, and the aqueous phase was extracted with 90 mL of toluene again. The resulting toluene phases were combined, washed with 90 mL of water, dried over anhydrous sodium sulfate, and concentrated under reduced pressure to obtain 4.776 g of yellow crystals. The resulting compound was analyzed by HPLC. Thereby, 3.17 g of the title compound was obtained (yield: 71%) ((2R, 3S)/(2S,3S)=92/8 (the diastereomeric ratio was measured by HPLC; HPLC conditions, column: CAPCELL PAK C18 TYPE MG manufactured by Shiseido Co. Ltd., mobile phase: acetonitrile/20 mM (potassium) phosphate buffer solution (pH=2.5)=2/8, flow rate: 1.0 mL/min, column temperature: 30° C., detector: UV 210 nm, retention time: 37 minutes (2R,3S), 41 minutes (2S,3S)).

Production Example 3

(2R,3S)-2-(2,5-Difluorophenyl)-3-methyl-2-[(1H-1,2,4-triazol-1-yl)methyl]oxirane A solution of 27.2 g (135.7 mmol) of (2R,3R)-1,2-epoxy-2-(2,5-difluorophenyl)butan-3-ol ((2R,3R)/(2S,3R)=93/7)/ 17.9 g (176.4 mmol) of triethylamine/225 mL of toluene was cooled in ice, and 20.3 g (176.4 mmol) of methanesulfonyl chloride was added thereto. The reaction was performed 2 hours. Then, 46 mL of water was added thereto, and subsequently 80 mL of a 5% aqueous solution of potassium hydroxide was added to stop the reaction. The organic phase was separated, dried over anhydrous sodium sulfate, and concentrated under reduced pressure to obtain 47.9 g of an oil.

A mixture of 29.8 g (154.5 mmol) of a 28% solution of NaOMe in methanol, 10.7 g (154.5 mmol) of triazole, and 111 mL of DMF was stirred at room temperature for 1 hour, and a solution of 47.9 g of the above-described crude mesylate in 134 mL of DMF was added at a time. The reaction was performed at 60° C. for 4 hours. Then, the resulting reaction solution was cooled to 0° C., and 650 mL of water was added dropwise to stop the reaction. Next, 900 mL of toluene was added, and the organic phase was separated. The aqueous phase was extracted with 900 mL of toluene again. The resulting toluene phases were combined, washed with 650 mL of water, dried over anhydrous sodium sulfate, and concentrated under reduced pressure to obtain 34.3 g of yellow crystals. The resulting compound was analyzed by HPLC. Thereby, 26.4 g of the title compound was obtained (yield: 82%) ((2R, 3S)/(2S,3S)=93/7 (the diastereomeric ratio was measured by HPLC; HPLC conditions, column: CAPCELL PAK C18 TYPE MG manufactured by Shiseido Co. Ltd., mobile phase: acetonitrile/20 mM (potassium) phosphate buffer solution (pH=2.5)=3/7, flow rate: 1.0 mL/min, column temperature: 30° C., detector: UV 210 nm, retention time: 14 minutes (2R,3S), 15 minutes (2S,3S))). $^1$H-NMR (400 MHz, CDCl$_3$) δ: 1.64 (d, 3H, J=5.6 Hz), 3.20 (q, 1H, J=5.6 Hz), 4.42 (d, 1H, J=14.6 Hz), 4.97 (d, 1H, J=14.6 Hz), 6.76-6.80 (m, 1H), 6.91-6.99 (m, 2H), 7.83 (s, 1H), 7.98 (s, 1H).

Production Example 4

(2R,3S)-3-(tert-Butyldimethylsilyloxy)-2-(2,4-difluorophenyl)-1-(1H-1,2,4-triazol-1-yl)butan-2-ol To a solution of 0.22 g (5.4 mmol) of sodium hydride (60% content) in 3 mL of DMF was added 0.37 g (5.4 mmol) of triazole. Furthermore, a solution of 0.63 g (1.8 mmol) of (2R,3S)-1-chloro-2-(2,4-difluorophenyl)-3-(tert-butyldimethylsilyloxy)butan-2-ol in 10 mL of DMF was added thereto. The resulting reaction mixture was stirred at room temperature for 2 hours and then at 50° C. for 12 hours. Next, 10 mL of water was added to stop the reaction, and extraction was performed with ethyl acetate (30 mL). After drying over anhydrous sodium sulfate, concentration was performed under reduced pressure to obtain a crude product. The resulting product was purified by column on silica gel to obtain 0.18 g of the title compound (yield: 25%). $^1$H-NMR (400 MHz, CDCl$_3$) δ: 0.22 (s, 6H), 0.97 (s, 12H), 4.42 (dq, 1H, J=5.9, 1.2 Hz), 4.54 (d, 1H, J=1.4 Hz), 4.81 (d, 1H, J=1.4 Hz), 6.67-6.78 (m, 2H), 7.32-7.38 (m, 1H), 7.71 (s, 1H), 7.96 (s, 1H).

Production Example 5

(2R,3S)-2-(2,4-Difluorophenyl)-1-(1H-1,2,4-triazol-1-yl)butane-2,3-diol

To a solution of 0.10 g of (2R,3S)-3-(tert-butyldimethylsilyloxy)-2-(2,4-difluorophenyl)-1-(1H-1,2,4-triazol-1-yl)butan-2-ol in 1 mL of THF was added 0.3 mL of TBAF (1 M) at room temperature. Stirring was performed at room temperature for 3.5 hours, and 5 mL of water was added thereto. Then, extraction was performed with ethyl acetate (30 mL). After drying over anhydrous sodium sulfate, concentration was performed under reduced pressure to obtain a crude product. The resulting product was purified by column on silica gel to obtain 0.61 g of the title compound (yield: 87%). $^1$H-NMR (400 MHz, CDCl$_3$) δ: 0.97 (d, 3H, J=6.3 Hz), 4.31 (q, 1H, J=6.3 Hz), 4.79-4.82 (m, 2H), 6.67-6.81 (m, 2H), 7.32-7.38 (m, 1H), 7.72 (s, 1H), 7.93 (s, 1H).

INDUSTRIAL APPLICABILITY

An intermediate for a triazole antifungal agent can be produced by an industrially safe process that can be easily operated from inexpensively available materials. Furthermore, an optically active epoxy alcohol derivative useful as an intermediate for, for example, pharmaceuticals such as an antifungal agent, can be produced. In addition, an optically active halohydrin derivative serving as an important intermediate for the epoxy alcohol derivative can be provided.

The invention claimed is:

1. A process for producing an optically active epoxy alcohol derivative represented by general formula (14):

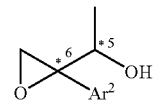

(14)

(wherein Ar$^2$ represents a substituted or unsubstituted aryl group having 6 to 20 carbon atoms; and each of *5 and *6 represents an asymmetric carbon), in all cases except where R$^3$ represents hydrogen, the process comprising:
subjecting a compound represented by general formula (6):

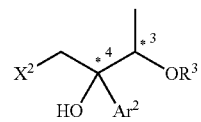

(6)

(wherein X$^2$ represents a halogen atom; R$^3$ represents hydrogen, a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, a substituted or unsubstituted acyl group having 1 to 20 carbon atoms, or a substituted or unsubstituted heterocycle; Ar$^2$ is the same as above; and each of *3 and *4 represents an asymmetric carbon) to at least one treatment selected from acid treatment, fluorine compound treatment, and hydrogenolysis to prepare an optically active halo diol derivative represented by general formula (13):

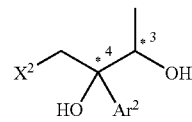

(13)

(wherein X$^2$, Ar$^2$, *3, and *4 are the same as above), and then treating the resulting halo diol derivative with a base; or in the case where R$^3$ represents hydrogen or a substituted or unsubstituted acyl group having 1 to 20 carbon atoms, the process comprising:
treating the compound represented by said general formula (6) with a base.

2. A process for producing an optically active halohydrin derivative represented by general formula (6):

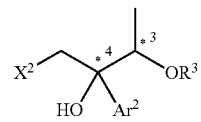

(6)

(wherein X$^2$ represents a halogen atom; R$^3$ represents hydrogen, a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, a substituted or unsubstituted acyl group having 1 to 20 carbon atoms, or a substituted or unsubstituted heterocycle; $Ar^2$ represents a substituted or unsubstituted aryl group having 6 to 20 carbon atoms; and each of *3 and *4 each represents an asymmetric carbon), the process comprising:

allowing an optically active haloketone derivative represented by general formula (4):

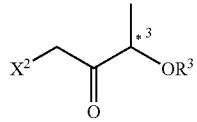

(4)

(wherein $x^2$, $R^3$, and *3 are the same as above) to react with a compound represented by general formula (5):

$Ar^2M^2$ (5)

(wherein $Ar^2$ is the same as above; and $M^2$ represents an alkali metal or a halogenated alkaline-earth metal).

3. The process according to claim 2, wherein the optically active haloketone derivative represented by said general formula (4) is prepared by allowing an optically active propionate compound represented by general formula (2);

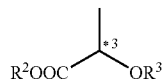

(2)

(wherein $R^2$ represents a substituted or unsubstituted alkyl group having 1 to 18 carbon atoms, a substituted or unsubstituted aryl group having 6 to 20 carbon atoms, or a substituted or unsubstituted aralkyl group having 7 to 20 carbon atoms; $R^3$ represents hydrogen, a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, a substituted or unsubstituted acyl group having 1 to 20 carbon atoms, or a substituted or unsubstituted heterocycle; and *3 represents an asymmetric carbon) to react with an enolate prepared by reaction of a haloacetic acid derivative represented by general formula (3):

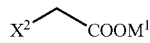

(3)

(wherein X2 is same as above; and M1 represents hydrogen, an alkali metal or a halogenated alkaline-earth metal) with a base, and then subjecting the resulting compound to acid treatment.

4. The process according to claim 3, wherein the base is tert-butylmagnesium chloride.

5. The process according to claim 3, wherein the compound represented by said general formula (2) is allowed to react with the compound represented by said general formula (3) in the presence of an amine.

6. The process according to claim 1, wherein the compound represented by said general formula (6) prepared by reacting a compound of general formula (4) with a compound of general formula (5) is used.

7. A process for producing an optically active halo diol derivative represented by general formula (13):

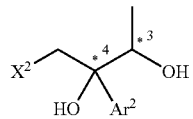

(13)

(wherein $X^2$ represents a halogen atom; $Ar^2$ represents a substituted or unsubstituted aryl group having 6 to 20 carbon atoms; and each of *3 and *4 represents an asymmetric carbon), the process comprising:

subjecting a compound represented by general formula (6a):

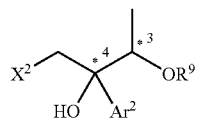

(6a)

(wherein $X^2$, $Ar^2$, *3, and *4 are the same as above; and $R^9$ represents a substituted or unsubstituted alkyl group having 1 to 18 carbon atoms, a substituted or unsubstituted aryl group having 6 to 20 carbon atoms, a substituted or unsubstituted aralkyl group having 7 to 20 carbon atoms, a substituted or unsubstituted silyl group, or a substituted or unsubstituted heterocycle) to at least one treatment selected from acid treatment, fluorine compound treatment, and hydrogenolysis.

8. A process for producing an optically active epoxide derivative represented by general formula (16):

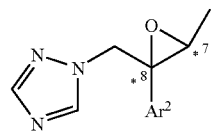

(16)

(wherein $Ar^2$ represents a substituted or unsubstituted aryl group having 6 to 20 carbon atoms; and each of *7 and *8 represents an asymmetric carbon), the process comprising:

allowing an optically active halo diol derivative represented by general formula (13):

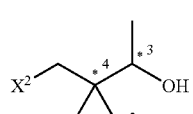

(13)

(wherein $X^2$ represents a halogen atom; $Ar^2$ is the same as above; and each of *3 and *4 represents an asymmetric carbon) to react with a compound represented by general formula (15):

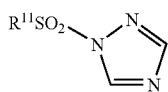 (15)

wherein R¹¹ represents a substituted or unsubstituted alkyl group having 1 to 18 carbon atoms, a substituted or unsubstituted aryl group having 6 to 20 carbon atoms, or a substituted or unsubstituted aralkyl group having 7 to 20 carbon atoms).

9. The process according to claim 8, wherein the compound represented by said general formula (13) prepared by the process of subjecting a compound of general formula (6a) to at least one treatment selected from acid treatment, fluorine compound treatment and hydrogenolysis is used.

* * * * *

UNITED STATES PATENT AND TRADEMARK OFFICE
CERTIFICATE OF CORRECTION

PATENT NO. : 7,582,781 B2
APPLICATION NO. : 10/563635
DATED : September 1, 2009
INVENTOR(S) : Okuro et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 903 days.

Signed and Sealed this

Fourteenth Day of September, 2010

David J. Kappos
*Director of the United States Patent and Trademark Office*